(12) United States Patent
Osmus et al.

(10) Patent No.: US 10,576,471 B2
(45) Date of Patent: Mar. 3, 2020

(54) FLUIDICS CARTRIDGE FOR USE IN THE VERTICAL OR SUBSTANTIALLY VERTICAL POSITION

(71) Applicant: ILLUMINA, Inc., San Diego, CA (US)

(72) Inventors: James Osmus, San Diego, CA (US); Richard L. Lemoine, San Diego, CA (US); Jian Gong, Danville, CA (US); Sz-Chin Steven Lin, Ladera Ranch, CA (US)

(73) Assignee: ILLUMINA, INC., San Diego, CA (US)

( * ) Notice: Subject to any disclaimer, the term of this patent is extended or adjusted under 35 U.S.C. 154(b) by 64 days.

(21) Appl. No.: 15/559,321

(22) PCT Filed: Mar. 18, 2016

(86) PCT No.: PCT/US2016/023227
§ 371 (c)(1),
(2) Date: Sep. 18, 2017

(87) PCT Pub. No.: WO2015/154038
PCT Pub. Date: Sep. 29, 2016

(65) Prior Publication Data
US 2018/0111126 A1    Apr. 26, 2018

Related U.S. Application Data

(60) Provisional application No. 62/136,345, filed on Mar. 20, 2015.

(51) Int. Cl.
*B01L 3/00*    (2006.01)

(52) U.S. Cl.
CPC ..... *B01L 3/502792* (2013.01); *B01L 3/50273* (2013.01); *B01L 3/502715* (2013.01);
(Continued)

(58) Field of Classification Search
CPC .. B01L 3/502792; B01L 3/5027; B01L 3/502; B01L 3/50; B01L 3/00
(Continued)

(56) References Cited

U.S. PATENT DOCUMENTS

| 6,210,891 B1 | 4/2001 | Nyren et al. |
| 6,258,568 B1 | 7/2001 | Nyren |

(Continued)

FOREIGN PATENT DOCUMENTS

| WO | 1991/06678 | 5/1991 |
| WO | 2002/080822 | 10/2002 |

(Continued)

OTHER PUBLICATIONS

Abdelgawad, et al., "All-terrain droplet actuation", Lab on a Chip, vol. 8, 2008, 672-677.
(Continued)

*Primary Examiner* — Christine T Mui
(74) *Attorney, Agent, or Firm* — Illumina, Inc.

(57) ABSTRACT

Disclosed herein are devices, systems and methods for conducting a reaction using electrowetting in a vertical or substantially vertical position. Some embodiments disclosed herein provide fluidic cartridges for use in a substantially vertical position comprising: (a) a front substrate; (b) a back substrate; (c) a droplet operations gap formed between the front substrate and the back substrate; and (d) a plurality of electrodes on the front substrate or the back substrate, wherein the plurality of electrodes are configured to transport a droplet along a substantially vertical plane defined by the front substrate and the back substrate.

27 Claims, 32 Drawing Sheets

(52) U.S. Cl.
CPC .............. B01L 2200/0673 (2013.01); B01L 2300/0627 (2013.01); B01L 2300/0809 (2013.01); B01L 2400/0427 (2013.01)

(58) Field of Classification Search
USPC .......................................... 422/502, 500, 50
See application file for complete search history.

(56) References Cited

U.S. PATENT DOCUMENTS

| | | | |
|---|---|---|---|
| 6,274,320 | B1 | 8/2001 | Rothberg et al. |
| 6,565,727 | B1 | 5/2003 | Shenderov et al. |
| 6,773,566 | B2 | 8/2004 | Shenderov et al. |
| 6,911,132 | B2 | 6/2005 | Pamula et al. |
| 6,977,033 | B2 | 12/2005 | Becker et al. |
| 7,001,792 | B2 | 2/2006 | Sauer et al. |
| 7,052,244 | B2 | 5/2006 | Fouillet et al. |
| 7,057,026 | B2 | 6/2006 | Barnes et al. |
| 7,163,612 | B2 | 1/2007 | Sterling et al. |
| 7,211,414 | B2 | 5/2007 | Hardin et al. |
| 7,315,019 | B2 | 1/2008 | Turner et al. |
| 7,328,979 | B2 | 2/2008 | Decre et al. |
| 7,329,492 | B2 | 2/2008 | Hardin et al. |
| 7,329,860 | B2 | 2/2008 | Feng et al. |
| 7,405,281 | B2 | 7/2008 | Xu et al. |
| 7,427,673 | B2 | 9/2008 | Balasubramanian et al. |
| 7,547,380 | B2 | 6/2009 | Velev |
| 7,641,779 | B2 | 1/2010 | Becker et al. |
| 7,727,466 | B2 | 6/2010 | Meathrel et al. |
| 8,039,817 | B2 | 10/2011 | Feng et al. |
| 8,241,573 | B2 | 8/2012 | Banerjee et al. |
| 2003/0132538 | A1 | 7/2003 | Chandler |
| 2003/0205632 | A1 | 11/2003 | Kim et al. |
| 2005/0100900 | A1 | 5/2005 | Kawashima et al. |
| 2005/0118574 | A1 | 6/2005 | Chandler et al. |
| 2005/0179746 | A1 | 8/2005 | Roux et al. |
| 2005/0260686 | A1 | 11/2005 | Watkins et al. |
| 2005/0277197 | A1 | 12/2005 | Chandler et al. |
| 2006/0039823 | A1 | 2/2006 | Yamakawa et al. |
| 2006/0159962 | A1 | 7/2006 | Chandler et al. |
| 2006/0164490 | A1 | 7/2006 | Kim et al. |
| 2006/0188901 | A1 | 8/2006 | Barnes et al. |
| 2006/0194331 | A1 | 8/2006 | Pamula et al. |
| 2006/0240439 | A1 | 10/2006 | Smith et al. |
| 2006/0281109 | A1 | 12/2006 | Barr Ost et al. |
| 2007/0023292 | A1 | 2/2007 | Kim et al. |
| 2007/0064990 | A1 | 3/2007 | Roth |
| 2007/0166705 | A1 | 7/2007 | Milton et al. |
| 2007/0207513 | A1 | 9/2007 | Sorensen et al. |
| 2008/0053205 | A1 | 3/2008 | Pollack et al. |
| 2008/0108082 | A1 | 5/2008 | Rank et al. |
| 2008/0124252 | A1 | 5/2008 | Marchand et al. |
| 2008/0151240 | A1 | 6/2008 | Roth |
| 2008/0283414 | A1 | 11/2008 | Monroe et al. |
| 2008/0305481 | A1 | 12/2008 | Whitman et al. |
| 2009/0026082 | A1 | 1/2009 | Rothberg et al. |
| 2009/0127589 | A1 | 5/2009 | Rothberg et al. |
| 2009/0192044 | A1 | 7/2009 | Fouillet |
| 2009/0272914 | A1 | 11/2009 | Feng et al. |
| 2009/0283407 | A1 | 11/2009 | Shah et al. |
| 2009/0321262 | A1 | 12/2009 | Adachi et al. |
| 2010/0096266 | A1 | 4/2010 | Kim et al. |
| 2010/0111768 | A1 | 5/2010 | Banerjee et al. |
| 2010/0137143 | A1 | 6/2010 | Rothberg et al. |
| 2010/0194408 | A1 | 8/2010 | Sturmer et al. |
| 2010/0282617 | A1 | 11/2010 | Rothberg |
| 2011/0048951 | A1 | 3/2011 | Wu |
| 2011/0104747 | A1 | 5/2011 | Pollack et al. |
| 2012/0270305 | A1 | 10/2012 | Williamson et al. |
| 2013/0079232 | A1 | 3/2013 | Kain et al. |
| 2013/0116128 | A1* | 5/2013 | Shen ................ B01L 3/502792 506/2 |
| 2013/0260372 | A1 | 10/2013 | Buermann et al. |
| 2013/0270114 | A1 | 10/2013 | Feiglin |

FOREIGN PATENT DOCUMENTS

| | | |
|---|---|---|
| WO | 2004/018497 | 3/2004 |
| WO | 2005/065814 | 7/2005 |
| WO | 2006/064199 | 6/2006 |
| WO | 2007/010251 | 1/2007 |
| WO | 2007/120241 | 10/2007 |
| WO | 2007/123744 | 11/2007 |
| WO | 2008/042067 | 4/2008 |
| WO | 2008/098236 | 8/2008 |
| WO | 2008/101194 | 8/2008 |
| WO | 2008/116221 | 9/2008 |
| WO | 2008/134153 | 11/2008 |
| WO | 2009/021173 | 2/2009 |
| WO | 2010/027894 | 3/2010 |
| WO | 2011/002957 | 1/2011 |
| WO | 2013/117595 | 8/2013 |
| WO | 2013/131962 | 9/2013 |

OTHER PUBLICATIONS

Bentley, et al., "Accurate whole human genome sequencing using reversible terminator chemistry", Nature, vol. 456, Nov. 2008, 53-59.

Cockroft, et al., "A single-molecule nanpore device detects DNA polymerase activity with single-nucleotide resolution", J. Am. Chem. Soc, 130(Jan. 3, 2008, 818-820.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Dhindsa, et al., "Virtual Electrowetting Channels: Electronic Liquid Transport with Continuous Channel Functionality", Lab on a Chip, vol. 10, 2010, 832-836.

Healy, "Nanopore-based single-molecule DNA analysis", Nanomed. 2(4), 2007, 459-481.

Korlach, et al., "Selective aluminum passivation for targeted immobilization of single DNA polymerase molecules in zero-mode waveguide nanostructures", PNAS, vol. 105 No. 4, 2008, 1176-1181.

Levene, et al., "Zero-Mode Waveguides for Single-Molecule Analysis at high concentrations", Science 299, 2003, 682-686.

Li, et al., "DNA molecules and configurations in a solid-state nanopore microscope", Nature Mater, 2(9), 2003, 611-615.

Lundquist, et al., "Parallel confocal detection of single molecules in real time", Opt. Lett. 33(9), 2008, 1026-1028.

Metzker, et al., "Emerging technologies in DNA sequencing", Genome Research, 15, 2005, 1767-1776.

Ronaghi, et al., "A Sequencing Method Based on Real-Time Phyrophosphate", Science 281 (5375), Jul. 1998, 363-365.

Ronaghi, et al., "Real-time DNA sequencing using detection of pyrophosphate release", Anal. Biochem. Nov. 1, 1996; 242 (1):84-9, Nov. 1996, 84-89.

Ronaghi, "Pyrosequencing sheds light on DNA sequencing", Genome Res, 11(1), 2001, 3-11.

Ruparel, et al., "Design and synthesis of a 3'-O-allyl photocleavable fluorescent nucleotide as a reversible terminator for DNA sequencing by synthesis", PNAS, 102, 2005, 5932-5937.

Soni, et al., "Progress toward Ultrafast DNA Sequencing Using Solid-State Nanopores", Clin Chem, 53(11), 2007, 1996-2001.

* cited by examiner

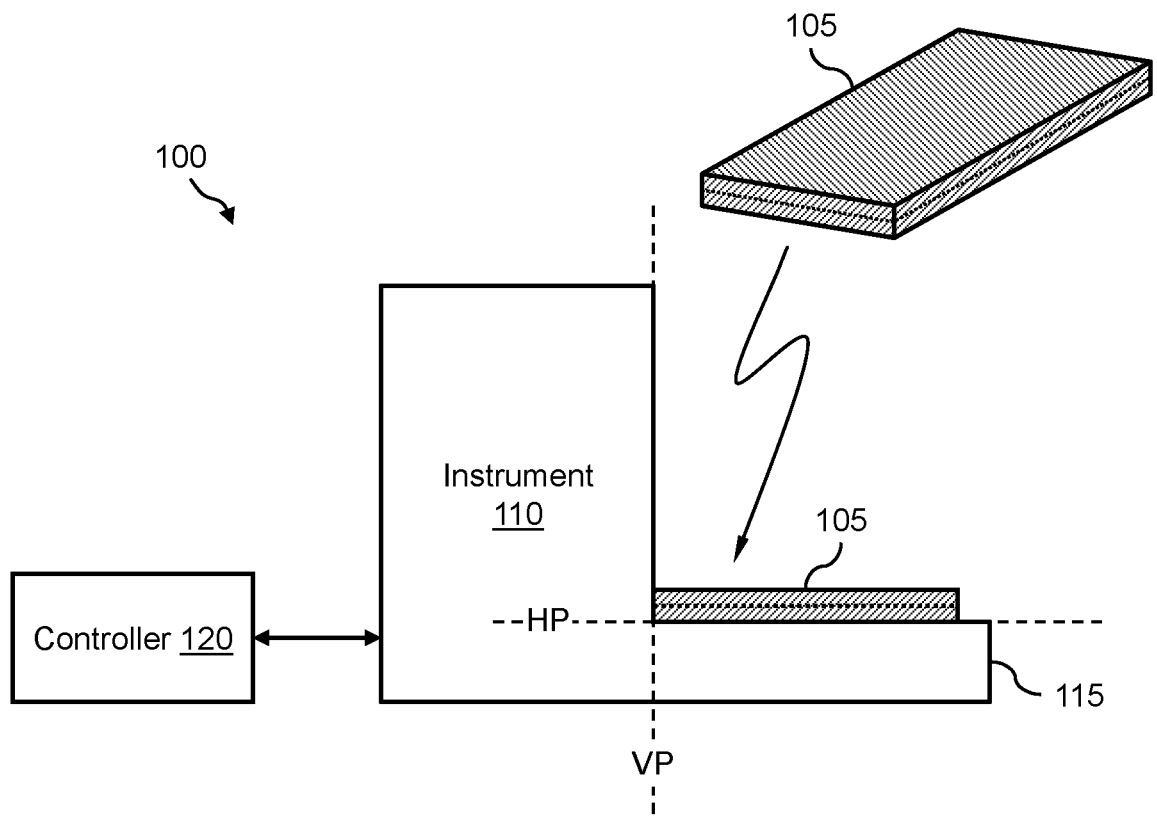
Figure 1A – PRIOR ART
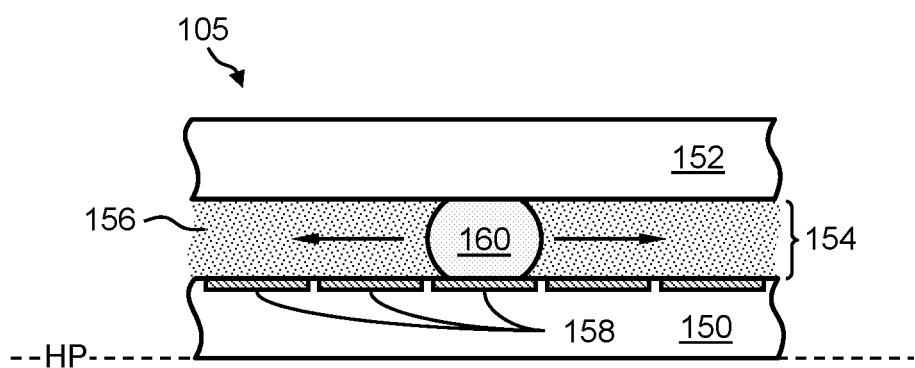
Figure 1B – PRIOR ART

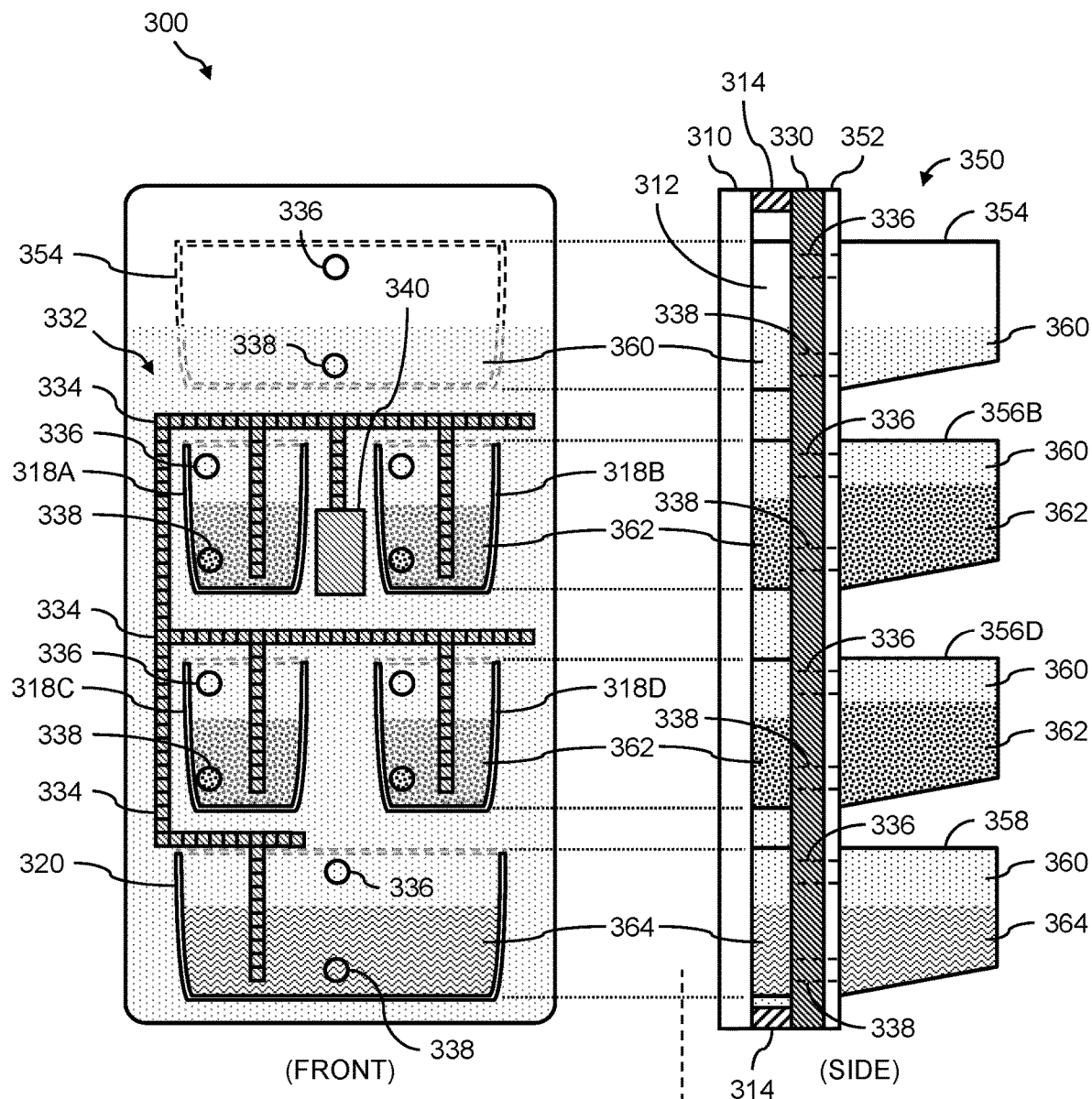
Figure 3A (FRONT) Figure 3B (SIDE)

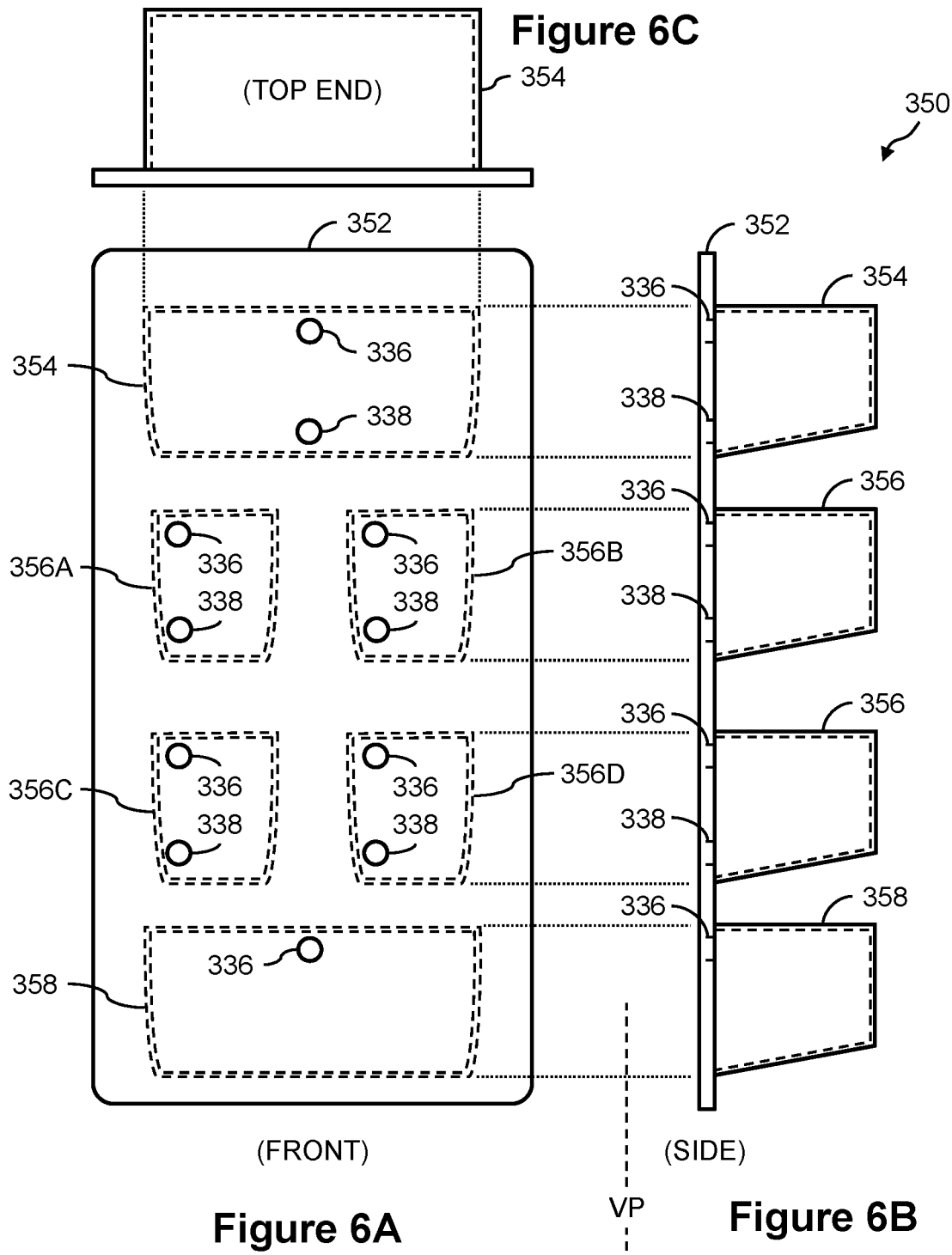

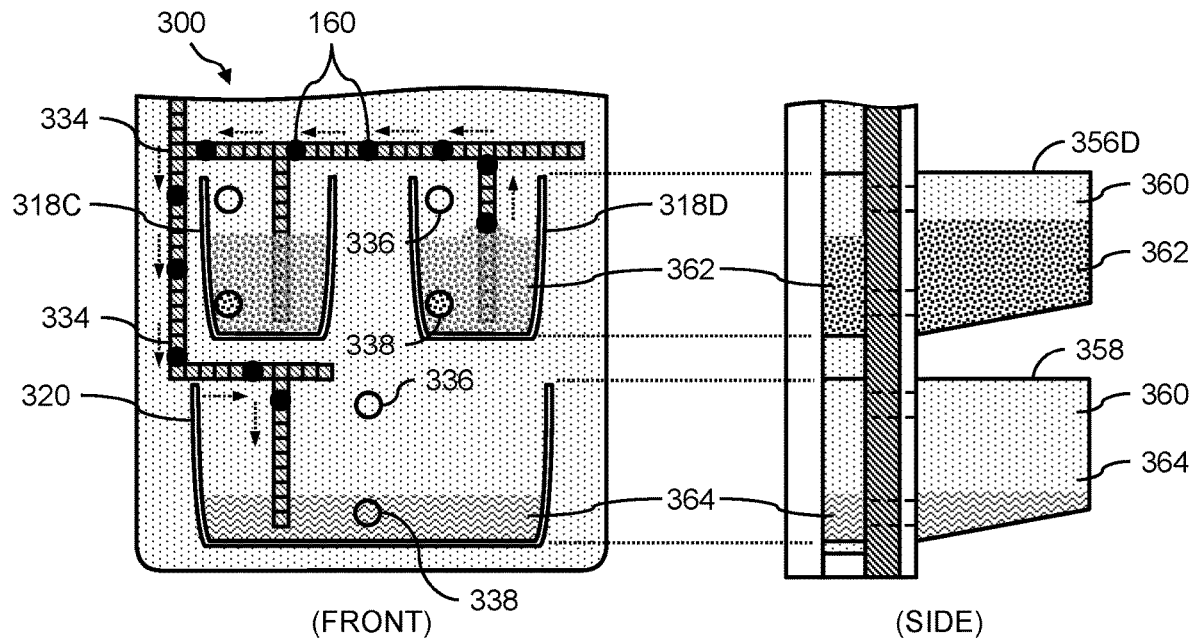
Figure 7A1        Figure 7A2
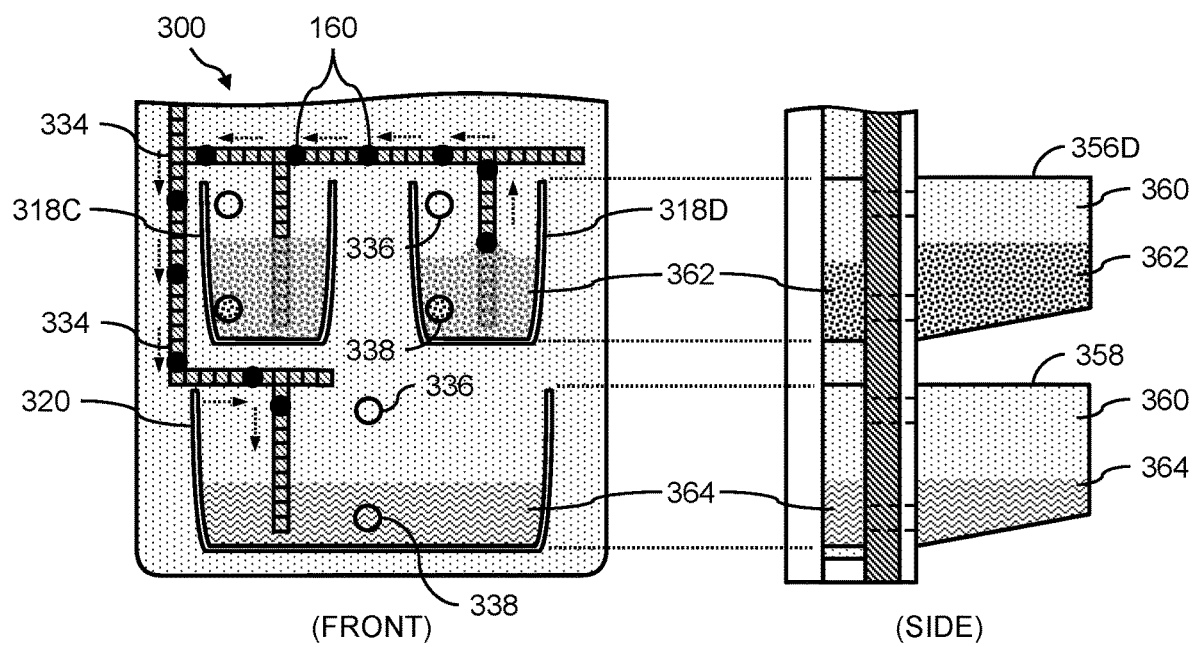
Figure 7B1        Figure 7B2

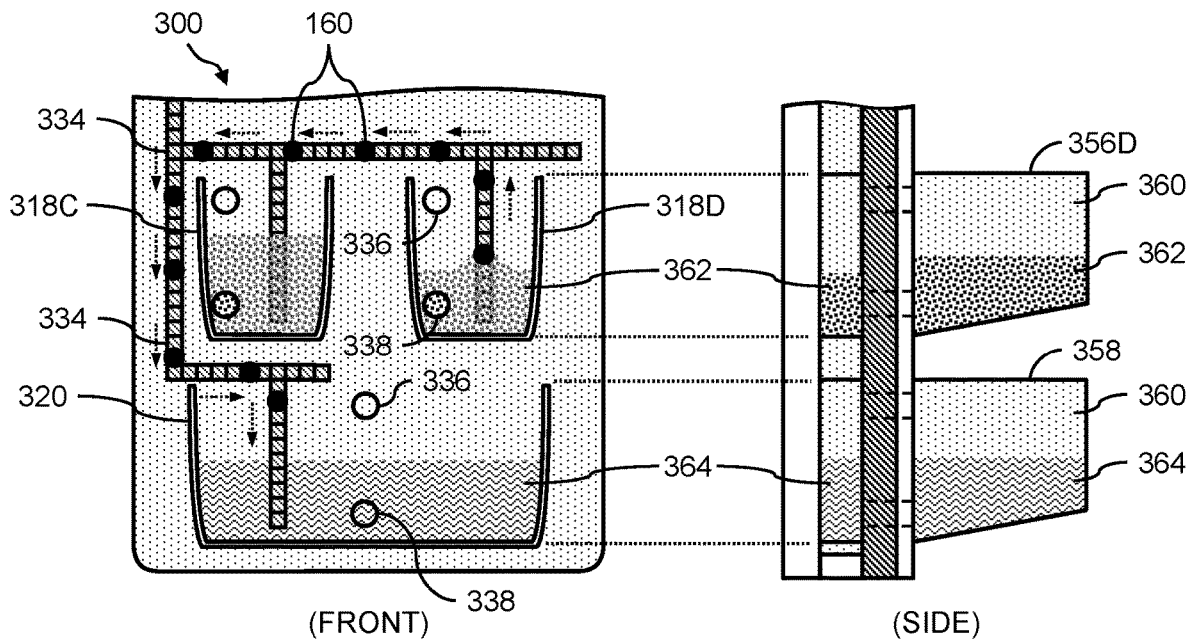
Figure 7C1  Figure 7C2
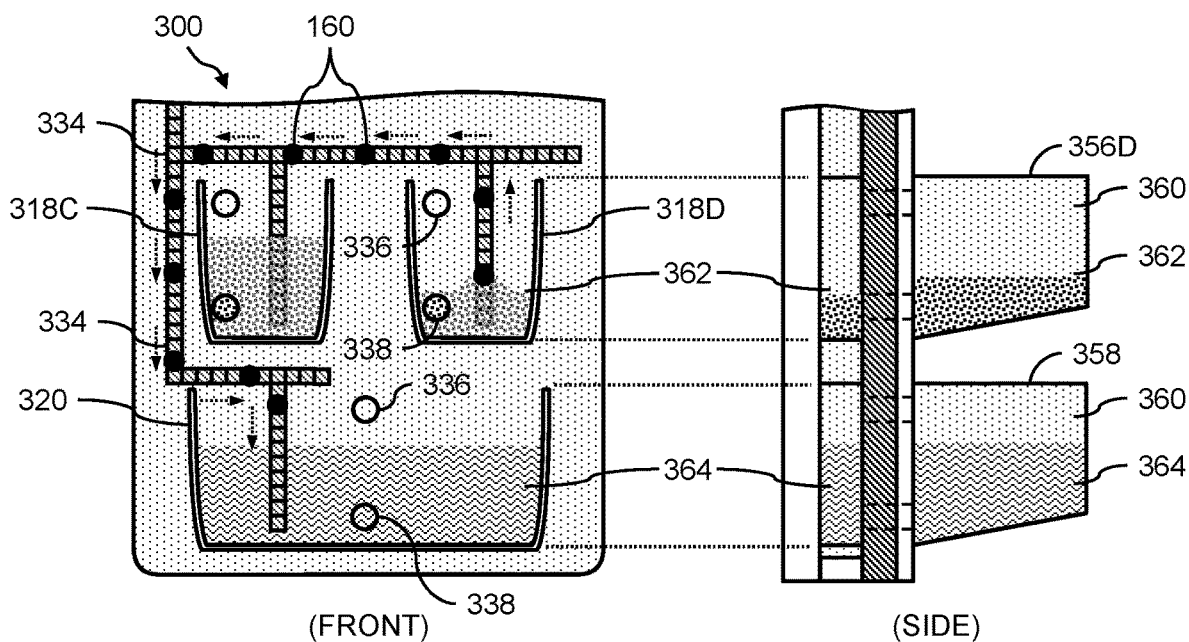
Figure 7D1  Figure 7D2

FLUIDICS CARTRIDGE FOR USE IN THE VERTICAL OR SUBSTANTIALLY VERTICAL POSITION

RELATED APPLICATIONS

This application is a U.S. National Stage Application of and claims priority to International Patent Application No. PCT/US2016/023227, filed on Mar. 18, 2016, which is based upon and claims the benefit of U.S. Provisional Patent Application Ser. No. 62/136,345, entitled "FLUIDICS CARTRIDGE FOR USE IN THE VERTICAL OR SUBSTANTIALLY VERTICAL POSITION," filed Mar. 20, 2015, each of which aforementioned applications is incorporated herein by reference in its entirety for all purposes.

BACKGROUND

Many types of fluidics technologies exist, and they are designed to move fluid from one location to another within a fluidics cartridge. Some fluidics cartridges use droplet actuators to move individual droplets within the fluidics cartridge, for example by electrowetting. An electrowetting fluidics cartridge is one example of a digital fluidics technology and typically includes one or more substrates configured to form a surface or gap which holds the reaction droplets that are moved from one location to another. The substrates establish a droplet operations surface, or gap, and can include electrodes arranged in predefined patterns to conduct the droplet operations via electrowetting. In some electrowetting devices, the gap between the substrates is filled with a filler fluid such as oil that is immiscible with the liquid that forms the droplets.

Conventional fluidics cartridges such as used in electrowetting devices are designed to be used in the horizontal position. However, a limitation exists for horizontal fluidics cartridges in that there is a head height restriction of about 3 mm. Thus, a reservoir for holding liquid reagents cannot generally be allowed to hold more than an approximately 3 mm height of liquid. When the height of the liquid becomes greater than about 3 mm in height, the pressure head of the liquid may exceed the force that an electrowetting pad can withstand, causing the reagent to flood the cartridge with liquid. In sequencing by synthesis (SBS) applications, large volumes of reagent (e.g., 50-80 ml) can be preferred. Spreading the large reagent volume over a reservoir area that is only about 3 mm high can consume a large amount of real estate in the fluidics cartridge.

FIG. 1A illustrates a block diagram of an example of a microfluidics system 100 that uses a prior art fluidics cartridge 105 held horizontally or substantially horizontally. In this example, microfluidics system 100 comprises an instrument 110 that has an instrument deck 115 for holding conventional fluidics cartridge 105. Conventional fluidics cartridge 105 can be, for example, any digital fluidics cartridge or droplet actuator cartridge by which droplets and/or volumes of liquid can be processed using droplet operations (e.g., electrowetting). Microfluidics system 100 further comprises a controller 120 for managing the overall operations of microfluidics system 100. Control information is passed from controller 120 to instrument 110 and instrument deck 115. Instrument 110 and instrument deck 115 provide the electrical, mechanical, and fluidic platform for interfacing with conventional fluidics cartridge 105. Associated with instrument 110 is a horizontal plane HP and a vertical plane VP wherein conventional fluidics cartridge 105 is held substantially in the horizontal plane HP. Referring now to FIG. 1B is a side view of a portion of an example of conventional fluidics cartridge 105 that is held substantially in the horizontal plane HP. Conventional fluidics cartridge 105 includes a bottom substrate 150 and a top substrate 152 that are separated by a droplet operations gap 154. Droplet operations gap 154 contains filler fluid 156. The filler fluid 156 is, for example, low-viscosity oil, such as silicone oil or hexadecane filler fluid. Bottom substrate 150 can be, for example, a printed circuit board (PCB) that may include an arrangement of droplet operations electrodes 158 (e.g., electrowetting electrodes). Top substrate 152 can be, for example, a plastic or glass substrate. Top substrate 152 may include a ground reference plane or electrode (not shown).

FIG. 1B shows a droplet 160 in droplet operations gap 154. Droplet operations are conducted atop droplet operations electrodes 158 on a droplet operations surface. Namely, in conventional fluidics cartridge 105, droplet operations are conducted along the horizontal plane HP. Conventional horizontally-mounted fluidics cartridges, such as conventional fluidics cartridge 105, are subject to the 3-mm head height restriction with respect to reservoirs (not shown). Further, conventional horizontally-mounted fluidics cartridges, such as conventional fluidics cartridge 105, are sensitive to tilt (not more than 1-2 degrees) and therefore not well suited for mobile applications. Additionally, in conventional horizontally-mounted fluidics cartridges the elimination of air bubbles can be difficult.

SUMMARY

Some embodiments disclosed herein provide fluidics cartridges for use in a substantially vertical position comprising: (a) a front substrate; (b) a back substrate; (c) a droplet operations gap formed between the front substrate and the back substrate; and (d) a plurality of electrodes on the front substrate or the back substrate, wherein the plurality of electrodes are configured to transport a droplet along a substantially vertical plane defined by the front substrate and the back substrate. In some embodiments, the front substrate or the back substrate is a printed circuit board (PCB). In some embodiments, the back substrate comprises one or more flow paths. In some embodiments, the fluidics cartridge comprises one or more reservoirs configured to hold a reagent, a filler fluid, a buffer, or a waste liquid. In some embodiments, the one or more reservoirs can hold a volume of 1-100 ml. In some embodiments, the one or more reservoirs are integrated into a plate to form a reservoir assembly. In some embodiments, each of the one or more reservoirs is in fluid communication with the droplet operations gap through a flow path. In some embodiments, each of the one or more reservoirs are in fluid communication with the droplet operations gap through an upper flow path and a lower flow path. In some embodiments, the one or more reservoirs comprise a U-shaped portion. In some embodiments, the height of the droplet operations gap at the position of a flow path is greater than the height of the droplet operations gap. In some embodiments, the front substrate comprises one or more U-features configured to hold a sample, a reaction mixture, a reagent, a filler fluid, a buffer, or a waste liquid. In some embodiments, a U-feature corresponds to a reservoir. In some embodiments, each of the one or more U-features comprises a U-shaped protrusion from an inside surface of the front substrate. In some embodiments, the U-shaped protrusion is porous. In some embodiments, the height of the U-shaped protrusion equals the height of the droplet operations gap. In some embodiments, the front substrate or back substrate comprises one or more downward dispensing volumes configured to hold a sample, a reaction mixture, a reagent, or a buffer. In some embodiments, the one or more downward dispensing volumes comprise sections having different heights. In some embodiments, the plurality of electrodes are configured to transport a droplet from the one or more U-features or the one or more downward dispensing volumes. In some embodiments, the plurality of electrodes are configured to form an electrowetting array. In some embodiments, the electrowetting array comprises a reagent dispense region, a reaction region, a sample loading region, a waste collection region, and a detection region. In some embodiments, the detection region comprises a CMOS detector. In some embodiments, the reaction region is configured to conduct a nucleic acid reaction selected from the group consisting of a PCR reaction, a sequencing reaction, a primer extension reaction and a clustering reaction.

Some embodiments disclosed herein provide methods of conducting a reaction using a fluidic cartridge, comprising: providing a reaction droplet to the droplet operations gap of the fluid cartridge; and actuating the reaction droplet to move vertically along the operations gap, wherein the fluidic cartridge is operated in a substantially vertical position. In some embodiments, the methods comprise drawing the reaction droplet by downward dispensing or upward dispensing. In some embodiments, the reaction droplet is about 25 uL to about 50 µL in volume. In some embodiments, the height of the droplet operations gap is about 325 µm. In some embodiments, the height of the droplet operations gap is about 950 µm. In some embodiments, the methods comprise merging a sample droplet and a reagent droplet to form the reaction droplet. In some embodiments, the reaction droplet comprises a nucleic acid molecule. In some embodiments, the reaction is a sequencing reaction, a primer extension reaction, or a clustering reaction. In some embodiments, the methods comprise activating a CMOS detector to detect a reaction product in the reaction droplet.

Some embodiments disclosed herein provide systems for conducting a reaction, comprising: a fluidic cartridge comprising a front substrate, a back substrate, and a plurality of electrodes configured to transport a droplet along a substantially vertical plane defined by the front substrate and the back substrate; and an instrument deck holding the fluidic cartridge in a substantially vertical position. In some embodiments, the front substrate or the back substrate is a printed circuit board (PCB). In some embodiments, the back substrate comprises one or more flow paths. In some embodiments, the fluidic cartridge comprises one or more reservoirs configured to hold a reagent, a filler fluid, a buffer, or a waste liquid.

Some embodiments disclosed herein provide methods for delivering reagents in a digital fluidics system, the method comprising: providing a first fluid and a second fluid in a detachable storage medium, wherein the first fluid has a first density and the second fluid has a second density, and wherein the detachable storage medium includes at least one temporary seal; attaching the detachable storage medium to the digital fluidics system, whereby at least one fluid connection forms between the detachable storage medium and the digital fluidics system, whereby the first fluid flows from the detachable storage medium to the digital fluidics system and an additional fluid flows from the digital fluidics system into the detachable storage medium, wherein the additional fluid has an additional density, and the additional density and the orientation of the detachable storage medium with respect to gravity causes at least a portion of the first fluid to exit the detachable storage medium through the fluid connection to a reservoir in the digital fluidics system; and charging at least one electrode in the digital fluidics system to transport droplets of the first liquid from the reservoir. In some embodiments, the first fluid is immiscible with the second fluid. In some embodiments, the first fluid comprises aqueous liquid and the second fluid comprises oil. In some embodiments, the transport of the droplets comprises digital fluidic movement of the droplets of the first fluid through the additional fluid. In some embodiments, the transport of the droplets comprises digital fluidic movement of the droplets in a direction opposite gravity. In some embodiments, the droplets comprise at least one reactant that participates in a nucleic acid reaction after being transported from the reservoir. In some embodiments, the additional fluid is the same type of fluid as the second fluid. In some embodiments, the second density is less than the additional density. In some embodiments, the additional density is less than the first density. In some embodiments, the methods further comprise using at least one electrode to change the temperature of the droplet. In some embodiments, the temperature change is sufficient to start a phase in a polymerase chain reaction procedure. In some embodiments, the methods further comprise splitting the droplet into two droplets and adding aqueous solution to each of the two droplets such that the two droplets each have a volume equivalent to the droplet. In some embodiments, the transport of the droplet comprises transport of at least a portion of the droplet into a nanowell. In some embodiments, a nucleic acid reaction takes place in the nanowell. In some embodiments, the digital fluidics system comprises a CMOS detector that detects a nucleic acid based on the nucleic acid reaction. In some embodiments, the methods further comprise washing the at least a portion of the droplet with additional fluid. In some embodiments, the methods further comprise air flowing into the detachable storage medium when the first fluid flows from the detachable storage medium to the digital fluidics system. In some embodiments, the air flows through an air vent. In some embodiments, the first fluid comprises materials required for a nucleic acid reaction. In some embodiments, forming the fluid connection comprises puncturing the temporary seal. In some embodiments, puncturing the temporary seal comprises using a microchip barb to pierce the temporary seal. In some embodiments, the temporary seal comprises a bubble wrap material. In some embodiments, forming the fluid connection comprises melting the temporary seal. In some embodiments, melting the temporary seal comprises using an electrode as a heating element. In some embodiments, melting the temporary seal comprises using an impedance as a heating element. In some embodiments, the temporary seal comprises a wax material. In some embodiments, the digital fluidics system comprises a collection zone, wherein the collection zone is configured to capture the wax material after melting. In some embodiments, the temporary seal includes a first magnet and a second magnet, wherein the first magnet and second magnet are polarized with opposing polarizations. In some embodiments, the first magnet is an electromagnet. In some embodiments, forming the fluid connection includes changing the polarity of the first magnet. In some embodiments, changing the polarity of the first magnet includes using an electrode to change the polarity of the first magnet. In some embodiments, the electromagnet includes a solenoid.

Some embodiments disclosed herein provide digital fluidic systems, comprising: an oil reservoir; a reagent reservoir; a cavity; a printed circuit board positioned to separate the cavity from the reservoirs, wherein the printed circuit board comprises a vertical face in contact with the cavity, wherein a first electrode and a second electrode are on the vertical face, wherein the cavity occurs along the vertical face between the printed circuit board and a cover, and wherein the first electrode and the second electrode are positioned to move a reagent droplet along the cavity opposite gravity based on the charges of the first electrode and the second electrode; a first gap in the printed circuit board that connects the reagent reservoir to the cavity; a second gap in the printed circuit board that connects the oil reservoir to the cavity; and a third gap in the printed circuit board that connects the reagent reservoir to the cavity, wherein the first gap is sealed with a first temporary sealing element and the second gap is sealed with a second temporary sealing element, the third gap is sealed with a third temporary sealing element, and wherein the second gap is above the third gap and the third gap is above the first gap. In some embodiments, the diameter of the first gap is between around 0.50 mm and around 1.00 mm in height. In some embodiments, the first gap is between around 1.01 mm and around 1.50 mm in height. In some embodiments, the first gap is between around 1.51 mm and around 2.81 mm. In some embodiments, the oil reservoir includes an oil with a density between around 0.79 g/mL and 0.90 g/mL. In some embodiments, the length through the printed circuit board of the first gap is approximately 0.01 mm longer than the length of the cavity. In some embodiments, the reagent reservoir is a U-cup shaped reservoir. In some embodiments, the reagent reservoir is a trapezoidal shaped reservoir. In some embodiments, the reagent reservoir has a height from the bottom of the reagent reservoir to the top of the reagent reservoir between approximately 54.0 mm and 56.0 mm. In some embodiments, the systems further comprise a third electrode, and wherein the first electrode, the second electrode, and the third electrode are positioned in a triangular pattern on the vertical face. In some embodiments, the systems further comprise an air vent in the digital fluidic system above the reagent reservoir, wherein the air vent is sealed with an air permeable, hydrophobic membrane, and wherein the air vent discharges to atmosphere. In some embodiments, the air vent is temporarily sealed with a wax. In some embodiments, the air vent is temporarily sealed with a film. In some embodiments, the cavity is cylindrical. In some embodiments, the systems further comprise a third electrode on the vertical face, and wherein the first electrode, the second electrode, and the third electrode are configured in a triangular arrangement on the vertical face. In some embodiments, the cavity is configured to contain more volume in the area around the first gap than in the area around the second gap.

Some embodiments disclosed herein provide modular containers, comprising: a cavity; a first entry to the cavity, wherein the first entry is sealable and wherein a reagent enters the cavity through the first entry; a second entry to the cavity, wherein the second entry is temporarily sealed with a second temporary seal and configured to allow an oil to enter the cavity through the second entry; a third entry to the cavity, wherein the third entry is temporarily sealed with a third temporary seal, and wherein the modular container is configured to connect to a digital fluidics system, and configured to allow the reagent to exit the cavity through the third entry, after the modular container connects to the digital fluidics system, based on gravity. In some embodiments, the second temporary seal and the third temporary seal are comprised of the same material. In some embodiments, the second temporary seal includes a wax with a melting point of about 45 degrees C. to about 60 degrees C.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates a block diagram of an example of a prior art microfluidics system that uses a conventional horizontally-mounted fluidics cartridge;

FIG. 1B illustrates a side view of a portion of an example of the prior art horizontally-mounted fluidics cartridge;

FIG. 3A illustrates a front view and FIG. 3B illustrates a side view of an example of the presently disclosed fluidics cartridge that can be used in the vertical or substantially vertical position;

FIG. 6A illustrates a front view, FIG. 6B illustrates a side view, and FIG. 6C illustrates a top end view of a reservoir assembly of the fluidics cartridge shown in FIGS. 3A,B;

FIGS. 7A1, 7A2, 7B1, 7B2, 7C1, 7C2, 7D1 and 7D2 illustrate a process of performing droplet operations on the presently disclosed fluidics cartridge that can be used in the vertical or substantially vertical position;

DETAILED DESCRIPTION

Overview

Figure 2A:
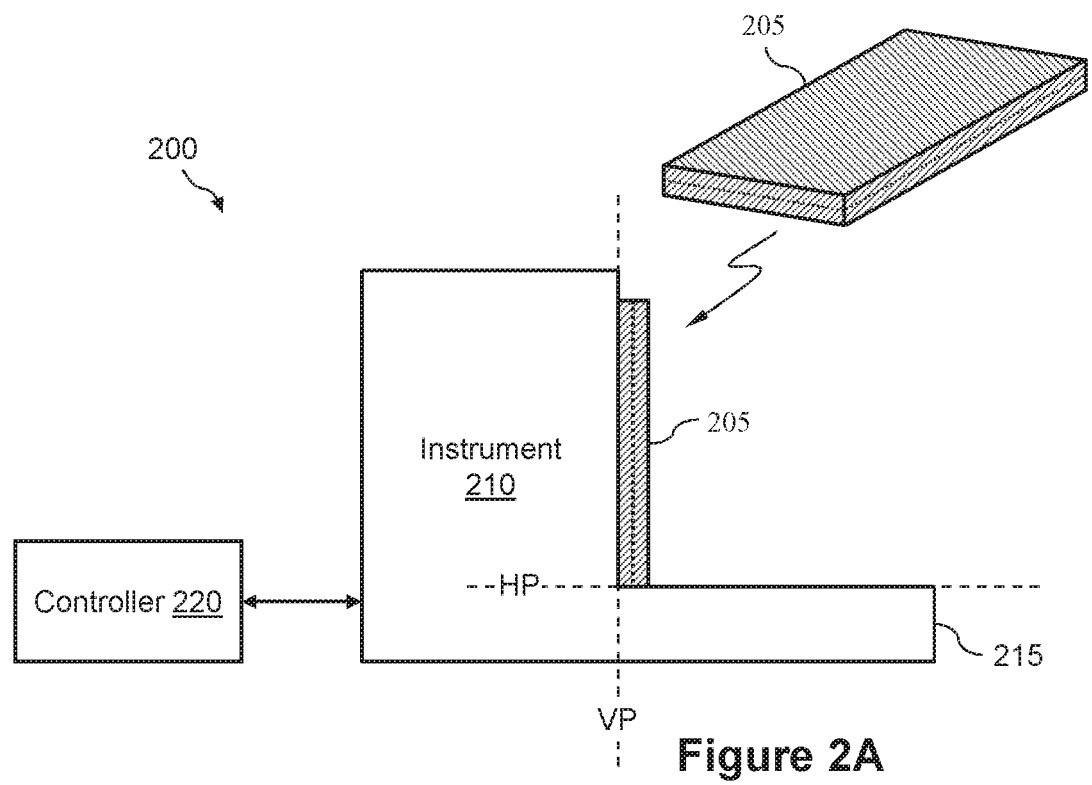
FIG. 2A illustrates a block diagram of an example of a microfluidics system that uses the presently disclosed fluidics cartridge that can be used in the vertical or substantially vertical position.

Embodiments of the invention include a digital fluidics system that is designed to hold a fluidics cartridge in a vertical, or substantially vertical position. The fluidics cartridge can have a front substrate, a back substrate and a droplet operations gap formed between the two substrates. A plurality of electrodes can be positioned on either the front substrate, back substrate or both. The digital fluidics system is designed so that the plurality of electrodes are capable of moving reaction droplets within the system along a vertical plane in addition to the horizontal plane. In one embodiment, this is accomplished by designing reaction wells within the vertical fluidics cartridge that do not flood the device when filled with fluid.

In one example, as discussed in more detail below, a reaction well may include a U-shaped bottom that has two arms in the vertical direction. One arm can be configured to hold a relatively large volume of fluid within one side of the well and the other arm can be configured to hold a relatively smaller volume of fluid next to an electrowetting pad in a more tapered arm. The smaller arm allows less fluid to contact the electrowetting pad, and prevents flooding within the device. In addition, the gap between the vertical plates is configured to balance the effects of gravity with the size and strength of the electrowetting pads such that droplets are capable of moving vertically within the device without gravity causing the droplets to stall or drop to lower positions.

Definitions

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms "a", "an", and "the" include plural references unless indicated otherwise, expressly or by context. For example, "a" droplet includes one or more droplets, unless indicated otherwise, expressly or by context.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers.

The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler, U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads.

Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference.

Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., *Nature* 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Fetermination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Ranket al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet actuator" is used to describe a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference.

Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates.

In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 μm, 100 μm, 200 μm, 250 μm, 275 μm or more. Alternatively or additionally the spacer height may be at most about 600 μm, 400 μm, 350 μm, 300 μm, or less. The spacer may, for example, be formed of a layer of projections form the top or bottom substrates, and/or a material inserted between the top and bottom substrates.

One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications.

In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap).

Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference.

One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.). Droplet transport voltage and frequency may be selected for performance with reagents used in specific assay protocols.

Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUORO-PEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan.

Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference.

Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid," "immiscible fluid" and "immiscible liquid" are used interchangeably to refer to a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200 C, viscosity=2.4 cSt, d=1.79), Galden HT230 (bp=230 C, viscosity=4.4 cSt, d=1.82) (all from Solvay Solexis); those in the Novec line, such as Novec 7500 (bp=128 C, viscosity=0.8 cSt, d=1.61), Fluorinert FC-40 (bp=155° C., viscosity=1.8 cSt, d=10.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc.

Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the present disclosure, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The terms "front," "back," "top," "bottom," "over," "under," and "on" are used throughout the description with reference to the relative positions of components of the fluidics cartridge, such as relative positions of top and bottom substrates or front and back substrates of the fluidics cartridge. It will be appreciated that the fluidics cartridge is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

The terms "fluidics cartridge," "digital fluidics cartridge," "droplet actuator," and "droplet actuator cartridge" as used throughout the description can be synonymous.

It is understood that aspects and embodiments of the disclosure described herein include "consisting" and/or "consisting essentially of" aspects and embodiments.

Other objects, advantages and features will become apparent from the following specification.

Fluidics Cartridge

Some embodiments disclosed herein provide fluidic cartridges for use in a substantially vertical position comprising: (a) a front substrate; (b) a back substrate; (c) a droplet operations gap formed between the front substrate and the back substrate; and (d) a plurality of electrodes on the front substrate or the back substrate, wherein the plurality of electrodes are configured to transport a droplet along a substantially vertical plane defined by the front substrate and the back substrate.

In some embodiments, the presently disclosed fluidics cartridge can be made to be used vertically or substantially vertically, or at an angle ranging from vertical (90 degrees) to greater than 0 degrees, or at an angle ranging from vertical (90 degrees) to about 45 degrees. FIG. 2A illustrates a block diagram of microfluidics system 200 using the presently disclosed fluidics cartridge 205 that can be used in the vertical or substantially vertical position. In this example, fluidics cartridge 205 is held substantially in the vertical plane VP. As shown in FIG. 2A, microfluidics system 200 further comprises instrument 210, instrument deck 215, and controller 220.

Figure 2B:
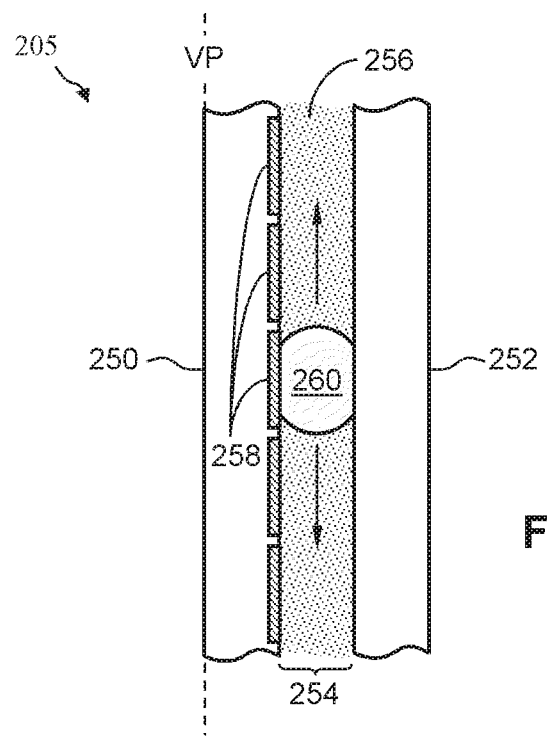
FIG. 2B illustrates a side view of a portion of an example of the presently disclosed fluidics cartridge that can be used in the vertical or substantially vertical position.
Figures 4A, 4B:
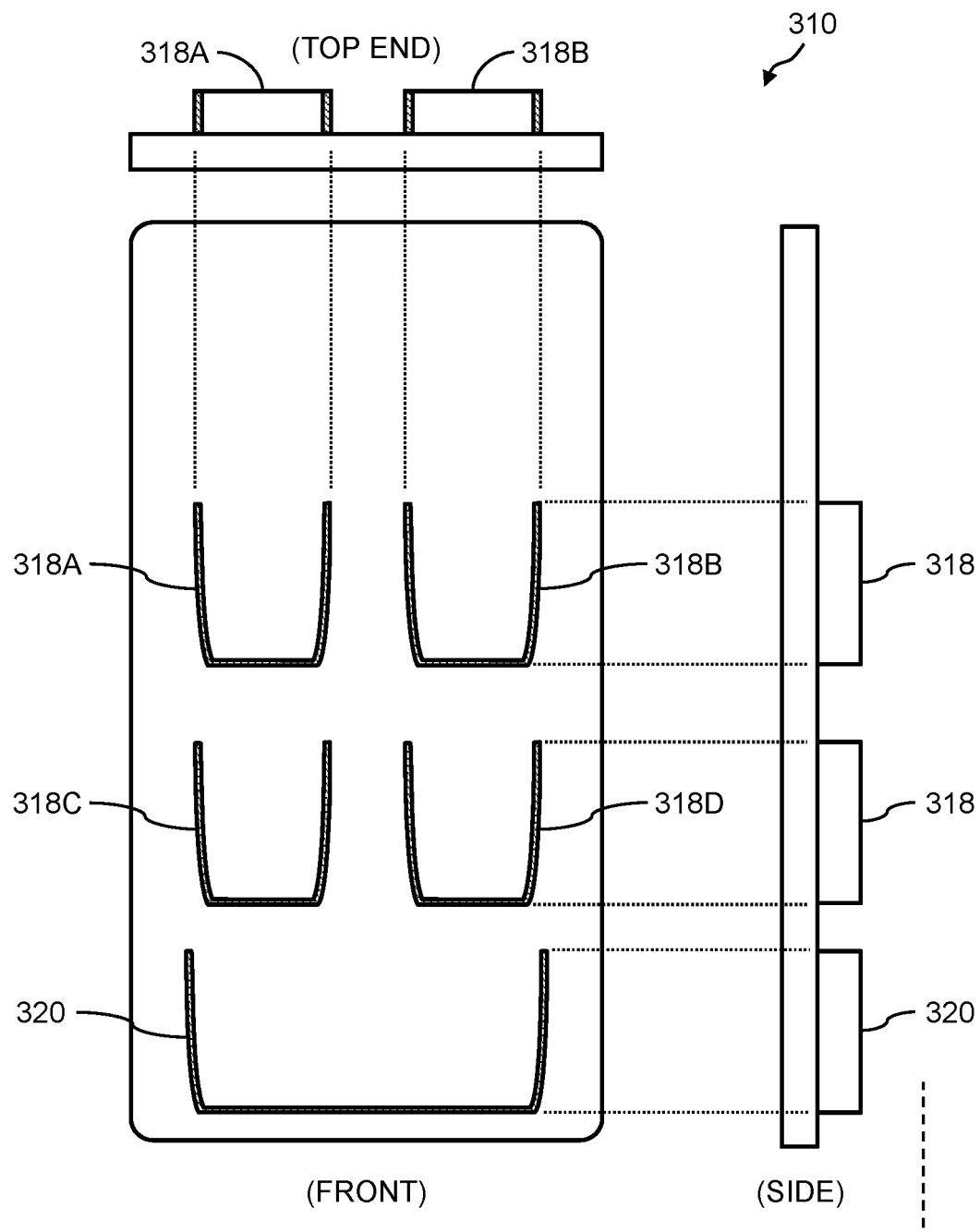
FIG. 4A illustrates a front view and FIG. 4B illustrates a side view, and a top end view of a front substrate of the fluidics cartridge shown in FIGS. 3A,B.

FIG. 2B is a cross-sectional side view of a portion of a fluidics cartridge 205 that can be used in the vertical or substantially vertical position. For example, fluidics cartridge 205 can be held substantially in the vertical plane VP. Fluidics cartridge 205 includes a back substrate 250 and a front substrate 252 that are separated by a droplet operations gap 254. Droplet operations gap 254 contains filler fluid 256. The filler fluid 256 is, for example, low-viscosity oil, such as silicone oil or hexadecane filler fluid. Back substrate 250 can be, for example, a PCB that may include an arrangement of droplet operations electrodes 258 (e.g., electrowetting electrodes). Front substrate 252 can be, for example, a plastic or glass substrate. Front substrate 252 may include a ground reference plane or electrode (not shown).

FIG. 2B shows droplet 260 in droplet operations gap 254. Droplet operations are conducted atop droplet operations electrodes 258 on a droplet operations surface. Namely, in fluidics cartridge 205, droplet operations are conducted along the vertical plane VP in droplet operations gap 254. Fluidics cartridges, such as fluidics cartridge 205, that can be used in the vertical or substantially vertical position are not sensitive to tilt and are therefore well suited for mobile applications. Further, fluidics cartridges, such as fluidics cartridge 205, can be used in the vertical or substantially vertical position are not subject to the 3-mm head height restriction with respect to reservoirs (not shown). This is because a volume of liquid can be held in a reservoir (not shown) in fluidics cartridge 205 and maintained in the reservoir by the force of gravity. Then, droplets are dispensed from the liquid volume in an upward fashion along the vertical plane VP (akin to drawing liquid upward in a straw). With a head height of liquid that can be significantly greater than 3 mm, the liquid is held by gravity in the reservoir and there is no propensity of the liquid to flood droplet operations gap 254. More details of the presently disclosed fluidics cartridge that can be used in the vertical or substantially vertical position are shown and described hereinbelow with reference to FIGS. 3-7.

With this embodiment, the about 3 mm head height restriction of conventional horizontally-mounted fluidics cartridges is eliminated because the liquid is at the bottom of the fluidics cartridge and then pulled upward. No matter the head height of the liquid, the liquid is held by gravity in the reservoir and there is no propensity of the liquid to flood the vertically-positioned droplet operations gap.

Yet another aspect is that the vertical fluidics cartridge can have a simpler front substrate as compared with the top substrate of a conventional horizontally-mounted fluidics cartridge. Horizontal cartridges sometimes may require the use of air vents to prevent trapping of air when the cartridge is initially filled with its filler fluid. In the vertical arrangement, the air rises to the top and these vents are not needed. In some embodiments, it may be preferable to include some topological features on the front substrate, such as a bulge opposite the port to allow for a quicker flow rate exiting the reservoir.

The fluidics cartridge may also be less sensitive to tilt than conventional horizontally-mounted fluidics cartridges. For example, in conventional horizontally mounted cartridges, if the cartridge is tilted sufficiently, liquid or fluid may spill out of the port or force the droplets in uphill ports to spill out unintentionally. The presently disclosed fluidics cartridge that can be used in the vertical or substantially vertical position substantially reduces or entirely eliminates this problem.

In addition, the fluidics cartridge described herein may have an easier time eliminating air bubbles as compared with conventional horizontally-mounted fluidics cartridges because the air bubbles naturally tend to float to the top of the vertical fluidics cartridge and exit to atmosphere.

In some embodiments, the fluidics cartridge includes a front substrate, a back substrate, and a reservoir assembly. The reservoir assembly comprises a plurality of off-cartridge reservoirs that rely on an aqueous/oil exchange process. Typically, a reservoir may contain a sample, a reagent, a buffer, a waste, or an immiscible liquid, and each reservoir correspond to one or more U-features or similarly configured structures in the droplet operations gap.

FIG. 3A illustrates a front view and FIG. 3B illustrates a side view of an example of the presently disclosed fluidics cartridge that can be used in the vertical or substantially vertical position. For example, FIG. 3A shows a fluidics cartridge 300 that is designed to be positioned vertically or substantially vertically, or at an angle ranging from vertical (90 degrees) to greater than 0 degrees, or at an angle ranging from vertical (90 degrees) to about 45 degrees. In this example, the fluidics cartridge 300 comprises a front substrate 310, a back substrate 330, and a reservoir assembly 350.

For the fluidic cartridges disclosed herein to function vertically or substantially vertically, structural features may be included as discussed below in the droplet operations gap to hold a liquid from which a droplet may be drawn, for example, a sample, a reagent, a buffer, or an immiscible liquid. In some embodiments, one or more U-features or similarly configured structures may be formed in the droplet operations gap. For example, a U-feature or similarly configured structure may comprise a protrusion from an inside surface of the front substrate or the back substrate, so that when the fluidic cartridge is in a vertical or substantially vertical position, a liquid is held in the space defined by the front substrate, the back substrate, and the U-feature or similarly configured structure in between. Therefore, the height of the protrusion may be the same as the height of the droplet operations gap, so that the liquid held in the U-feature or similarly configured structure will not leak. The height of protrusion can be from about 0.4 mm to about 3 mm in one example, or from about 0.4 mm to about 1.2 mm in another example, or is about 0.7 mm in yet another example. In some embodiments, the protrusion may be porous.

Referring now to FIGS. 3A and 3B, front substrate 310 and back substrate 330 are separated by a droplet operations gap 312. Droplet operations gap 312 can be set, for example, using one or more spacers 314 arranged between front substrate 310 and back substrate 330. Droplet operations gap 312 contains filler fluid 360 when in operation. The filler fluid 360 is, for example, low-viscosity oil, such as silicone oil or hexadecane filler fluid. Front substrate 310 can be, for example, a molded plastic or glass substrate. Front substrate 310 may include a ground reference plane or electrode (not shown). Back substrate 330 can be, for example, a PCB that includes an electrode arrangement 332 of droplet operations electrodes 334 (e.g., electrowetting electrodes).

Front substrate 310 includes a set of U-features that correspond to the four reagent reservoirs 356 and waste reservoir 358 of reservoir assembly 350. These U-features are also shown more clearly with reference to FIGS. 4A and 4B. Namely, front substrate 310 includes a set of four reagent U-shaped features 318A, 318B, 318C, 318D that substantially corresponds in size, shape, and position to the set of four reagent reservoirs 356 of reservoir assembly 350. Front substrate 310 further includes a waste U-feature 320 that substantially corresponds in size, shape, and position to waste reservoir 358 of reservoir assembly 350. While the term "reagent" is used with reference to reagent U-features 318 and reagent reservoirs 356, these U-features and reservoirs are not limited to holding reagent liquid only. Reagent U-features 318 and reagent reservoirs 356 can be used to hold any type of liquid.

Each of the U-features is a U-shaped protrusion from the surface of front substrate 310 that is facing droplet operations gap 312. The height of each U-shaped protrusion substantially corresponds to the height of droplet operations gap 312 so that the U-features can be tightly fitted against the surface of back substrate 330 with no fluid leakage. For example, by making the U-shaped protrusion and a dielectric substrate hydrophobic, a small gap can be tolerated without leaking fluid. The height of droplet operations gap 312 can be from about 0.4 mm to about 3 mm in one example, or from about 0.4 mm to about 1.2 mm in another example, or is about 0.7 mm in yet another example. The height of reagent U-features 318 and waste U-feature 320 shown in FIGS. 3A and 3B is not drawn to scale.

Each of the U-features provides a cup-like structure for holding a volume of liquid in droplet operations gap 312. In the presently disclosed fluidics cartridge, such as fluidics cartridge 300, droplets can be dispensed from the top surface of the liquid in these cup-like structures and transported (via droplet operations) upward and away from the volume of liquid. The presently disclosed fluidics cartridge relies on an aqueous/oil exchange process for automatically displacing aqueous liquid with filler fluid or filler fluid with aqueous liquid in the U-features and/or in the off-cartridge reservoirs. Further, the filling of the reagent into the filler fluid is driven by capillary forces and gravity.

Figure 29A:
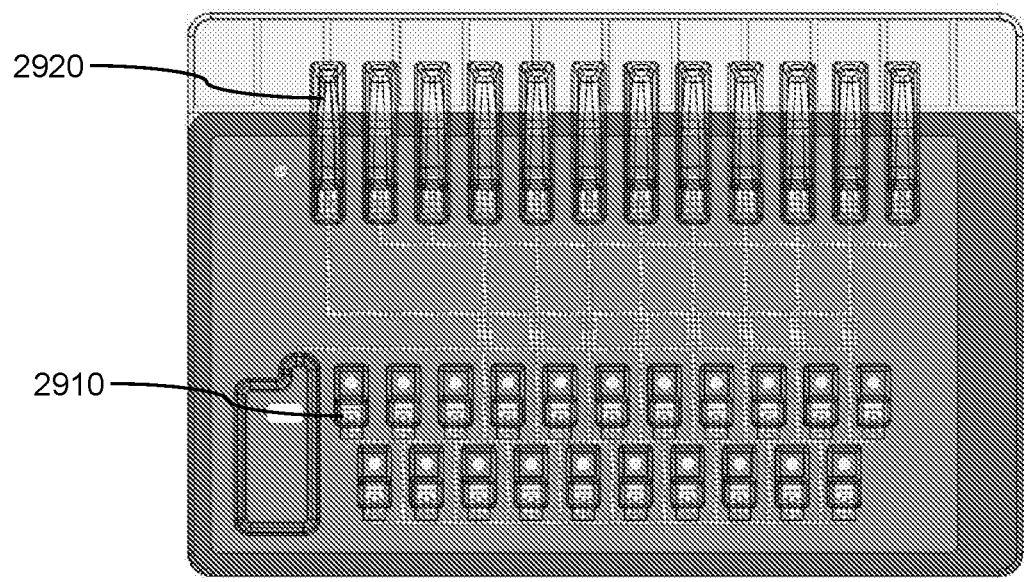
FIGS. 29A and 29B illustrate an exemplary fluidics cartridge having multiple downward dispensing volumes, some of which are connected to loading ports on top.
Figure 29B:
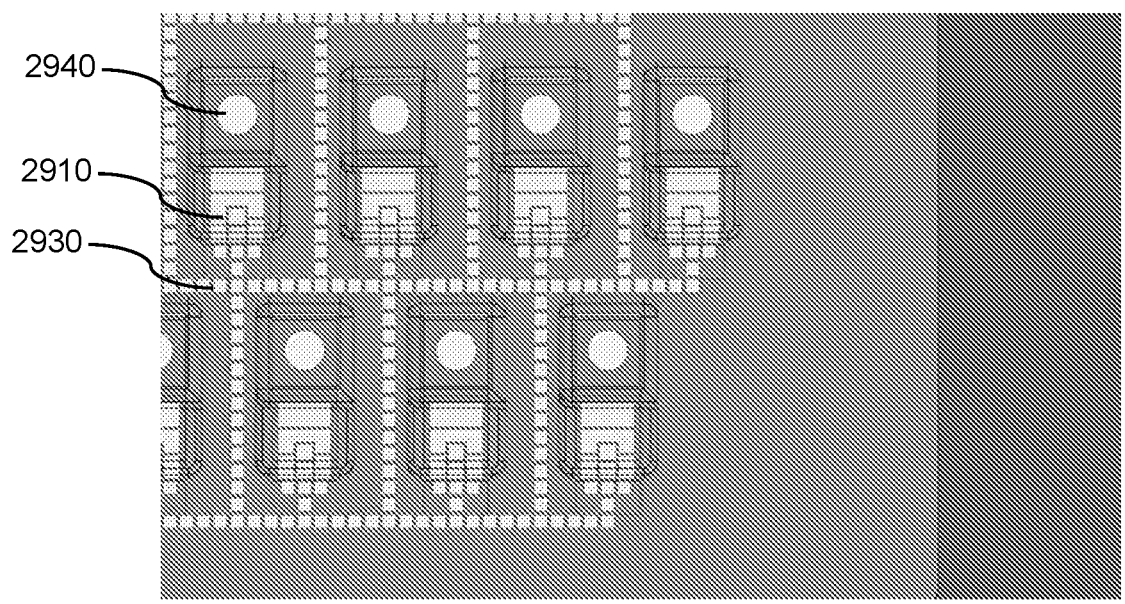

In some embodiments, the fluidics cartridges disclosed herein may comprise one or more structural elements for holding a small volume of liquid in the droplet operations gap for downward dispensing a droplet as described elsewhere in this disclosure. As shown in FIG. 29A, a plurality of downward dispensing volumes 2910 may be included in the fluidics cartridge. In some embodiments, the downward dispensing volumes 2910 may be connected to a sample loading port 2920. FIG. 29B shows an enlarged view of part of the fluidics cartridge of FIG. 29A, which illustrates downward dispensing volumes 2910, the electrodes 2930, and the flow path 2940. In some embodiments the downward dispensing volumes 2910 may be connected to a blister, a reservoir or a sample loading port through the flow path 2940.

Figure 30:
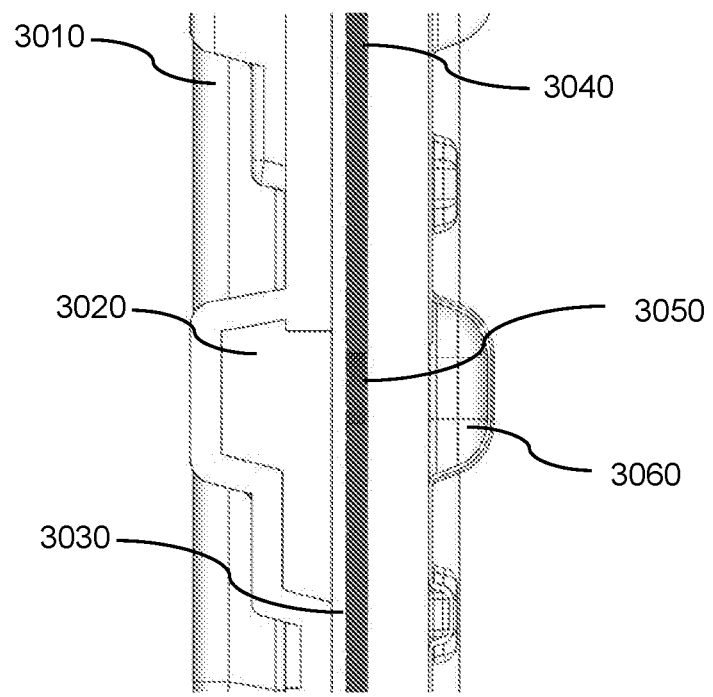
FIG. 30 shows a sectional view of a downward dispensing volume that is built into the front plate and connected to a blister on the back plate.

FIG. 30 shows a sectional view of a downward dispensing volume 3020 that is part of the front substrate 3010. In some embodiments, the downward dispensing volume may be part of the back substrate, or both the front and back substrates. The dispensing volume may be connected to a blister 3060, or a reservoir that is integrated to the back substrate 3040 through the flow path 3050. In some embodiments, the downward dispensing volume 3020 may comprise two or more sections having different gap heights to allow a stepwise downward dispensing of a droplet into the droplet operations gap 3030.

Figure 28A:
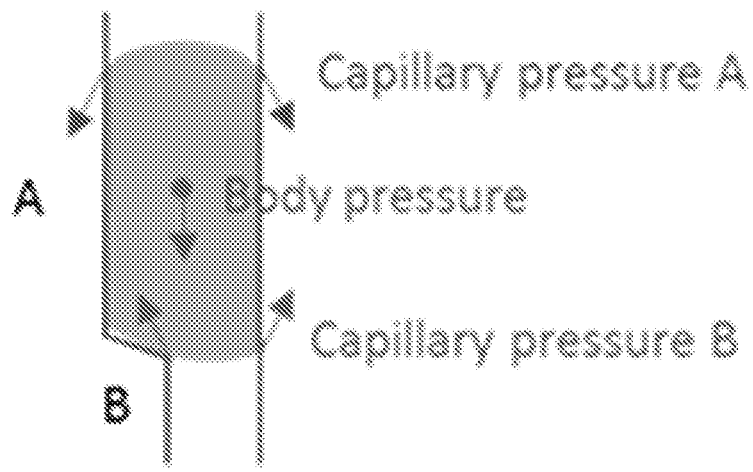
FIGS. 28A and 28B illustrate exemplary configurations for step-wise downward dispensing.

As shown in FIG. 28A, a downward force from the pressure head of the reagent in the downward dispensing volume, referred to as the body pressure, is resisted by the upward capillary force due to interfacial tension, referred to as capillary pressure B. There is also a downward capillary pressure at the top of the downward dispensing volume called capillary pressure A. By design the gap height at the top of a downward dispensing volume is larger than the dispense region at the exit of the downward dispensing volume. By this arrangement capillary pressure B is greater in magnitude than capillary pressure A, which prevents flooding of the cartridge by the reagent in the downward dispensing volume. In some embodiments, the gap heights of Step A and Step B are 3 mm and 1 mm, respectively.

Figure 28B:
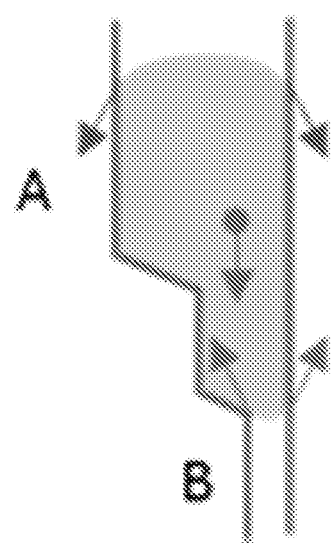

When electrodes at dispense region at the exit of the downward dispensing volume are energized to dispense, the contact angle at B is reduced. Force balances between body pressure and capillary forces can be calculated in passive and energized states. As long as the direction of the net force remains upward, the reagent can be stored in the downward dispensing volume without flooding the cartridge during passive storage or active dispensing. In a three-step layout as shown in FIG. 28B, the middle gap height can be set close to the step A gap so the reagents passively enter (flood) the middle gap height or closer to the smaller step B gap so electrowetting may be used to move the reagent into the middle gap. In some embodiments, the gap heights of Step A, Step X and Step B are: 3 mm, 1 mm and 0.43 mm, respectively, or 3 mm, 1.34 mm and 0.43 mm, respectively.

For downward dispensing, the downward dispensing volume may be optimized to avoid flooding of the cartridge. In some embodiments, the downward dispensing volume may be about 10 µL, 20 µL, 30 µL, 40 µL, 50 µL, 60 µL, 70 µL, 80 µL, 90 µL, 100 µL, 200 µL, 300 µL, 400 µL, 500 µL, 1 mL, 10 mL, 100 mL, or a range between any two of the above-mentioned values. One advantage of downward dispensing is the ability to minimize the amount dead volume. In some embodiments, the dead volume in a downward dispensing volume can be about 50 µL, 40 µL, 30 µL, 20 µL, 10 µL, 5 µL, 4 µL, 3 µL, 2 µL, 1 µL or less.

In some embodiments, droplets of fluid are electrically manipulated in the droplet operations gap by an array of electrodes located on the front substrate, the back substrate, or both. In a commonly used configuration, the droplets are sandwiched between the front substrate and the back substrate where the back substrate contains an array of individually addressable drive or control electrodes which are electrically insulated. Typically, one or more reference electrodes are also used to control the electrical potential of the droplet. Reference electrodes may be either provided on the same substrate as the drive electrodes (co-planar) or on an opposite plate (bi-planar). The space between the two substrates surrounding the droplet is generally open and may be filled with air or with an immiscible liquid to prevent evaporation. Examples of immiscible liquids that may be used with aqueous droplets include silicone oil, fluorosilicone oil or hydrocarbon oils. When the reference electrodes and drive electrodes are provided on the same substrate, the opposing plate does not serve as part of the electrical circuit, but serves only as a cover plate to physically contain the liquids and may not be required for operation of the device.

Referring now to FIGS. 3A 3B, electrode arrangement 332 of back substrate 330 includes multiple lines or paths of droplet operations electrodes 334 that are fluidly connected. For example, electrode arrangement 332 includes certain lines or paths of droplet operations electrodes 334 that run up and down on back substrate 330 as well as certain lines or paths of droplet operations electrodes 334 that run side-to-side on back substrate 330, as shown. These lines or paths of droplet operations electrodes 334 provide fluid paths in and out of reagent U-features 318A, 318B, 318C, 318D and waste U-feature 320. Further, a line or path of droplet operations electrodes 334 is provided to a CMOS detector 340 that is mounted on back substrate 330. In one example, CMOS detector 340 is an optical detector.

In some embodiments, the front substrate or the back substrate may comprise a printed circuit board (PCB), also sometimes called a printed wiring board (PWB). PCB is a substrate used to interconnect electronic components using conductive pads and traces patterned on the substrate. Typically, PCBs are made by adhering a layer of copper over the entire substrate, sometimes on both sides, (known as creating a "blank PCB") then removing unwanted copper (e.g., by etching in an acid) after applying a temporary mask, leaving only the desired copper traces. Electrical connections ("vias") between opposite sides of the substrate can be formed by drilling holes through the substrate either mechanically or with a laser and metallizing the interior of the drill hole to provide a continuous electrical connection between the two sides. Multilayer boards can be created by bonding together individually processed substrates. Electrode lines in the copper layer are usually defined by etching copper from a blank PCB in a subtractive process while some foundries use semi-additive and fully-additive processes where copper is built up on the substrate by electroplating or other techniques.

Figures 5A, 5B:
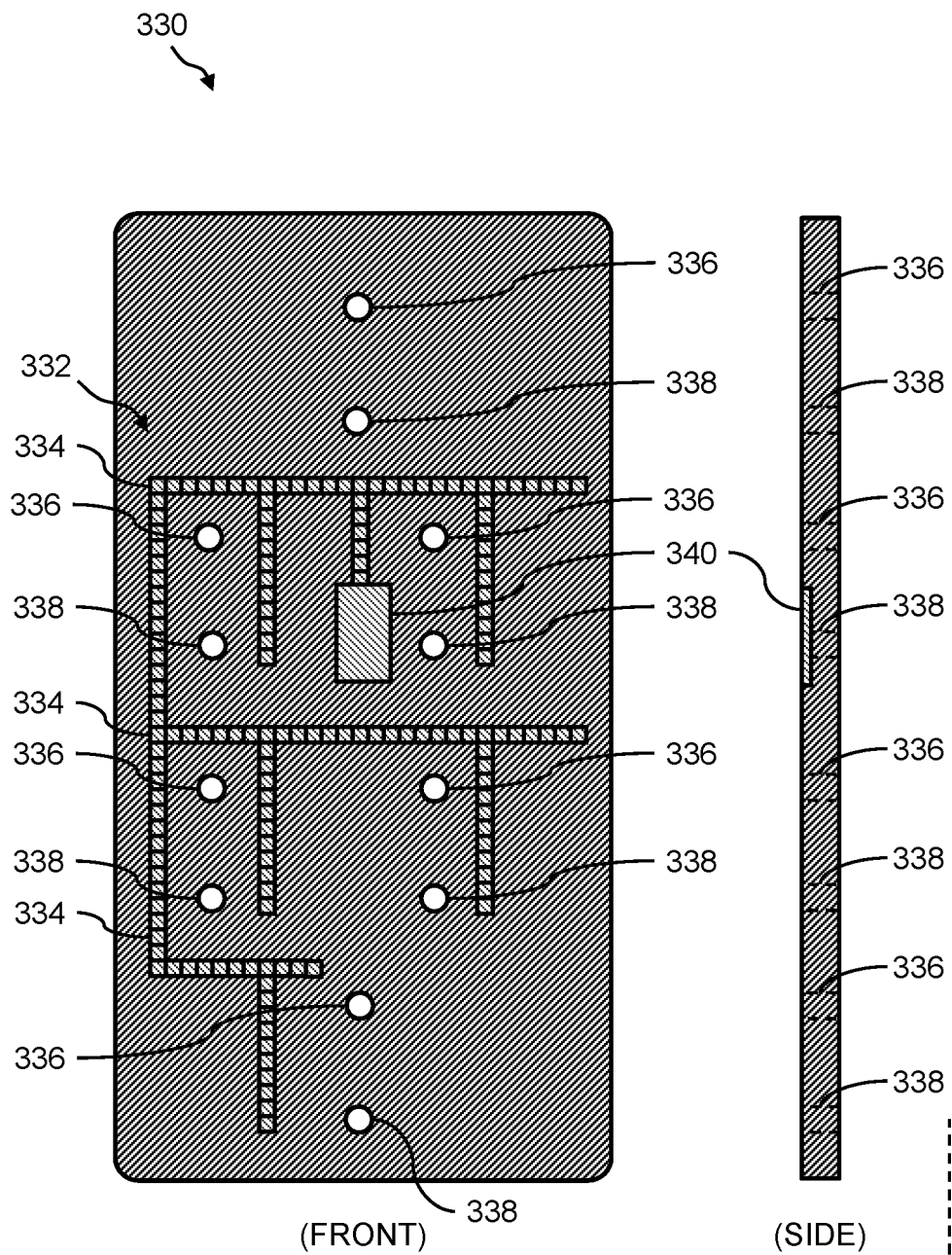
FIG. 5A illustrates a front view and FIG. 5B illustrates a side view of a back substrate of the fluidics cartridge shown in FIGS. 3A,B.

In some embodiments, the array of electrodes may be arranged on the back substrate as shown in FIGS. 5A and 5B. The array of electrodes may define one or more paths that control the movement of droplets. For example, droplets may be drawn from a liquid contained in one for more of the U-features and moved along the electrodes of the electrowetting array. In some embodiments, the electrowetting array may comprise one or more droplet operations regions, e.g., a reagent dispense region, a reaction region, a sample loading region, a waste collection region, a detection region, etc.

Figure 10:
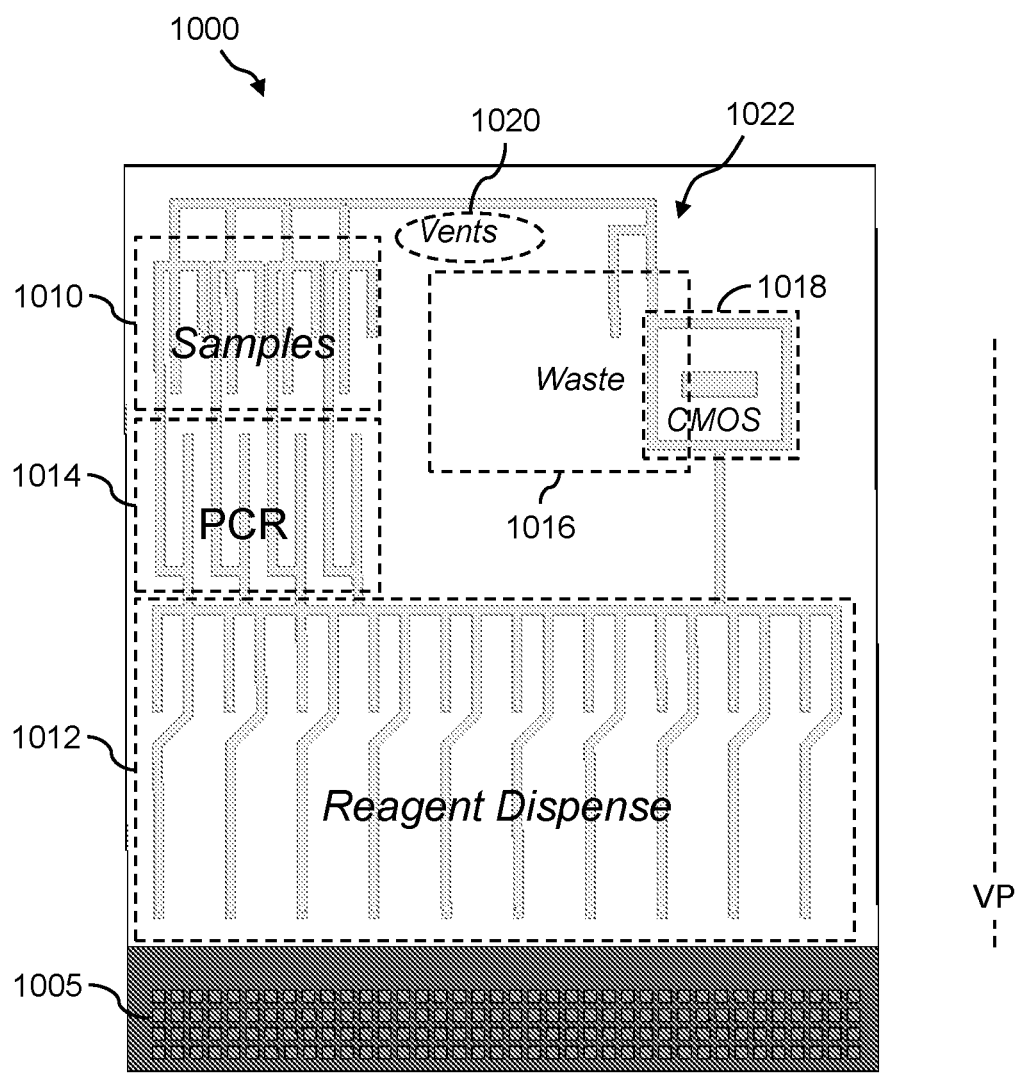
FIGS. 10 and 11 illustrate a front view and a back view, respectively, of another example of the presently disclosed fluidics cartridge that can be used in the vertical or substantially vertical position.
Figure 11:
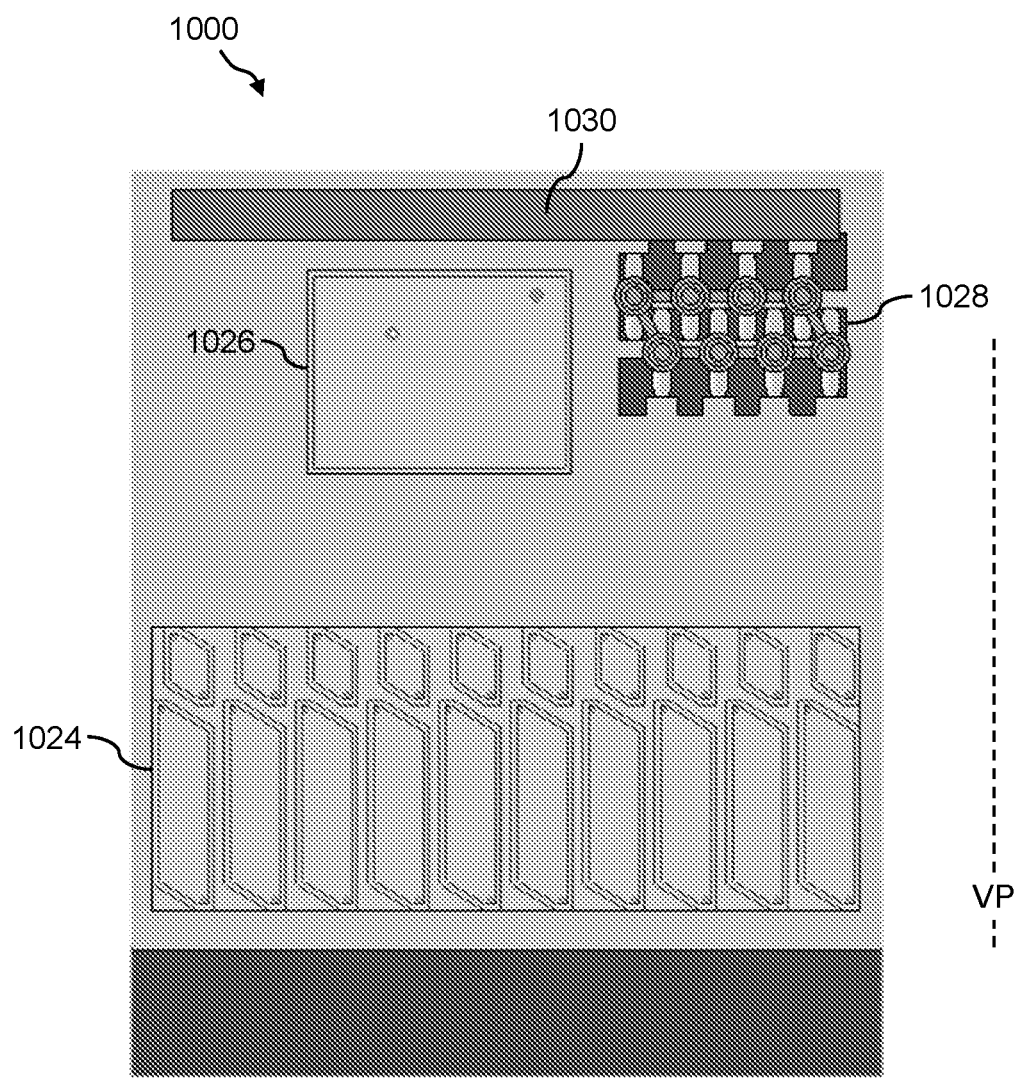
Figure 12:
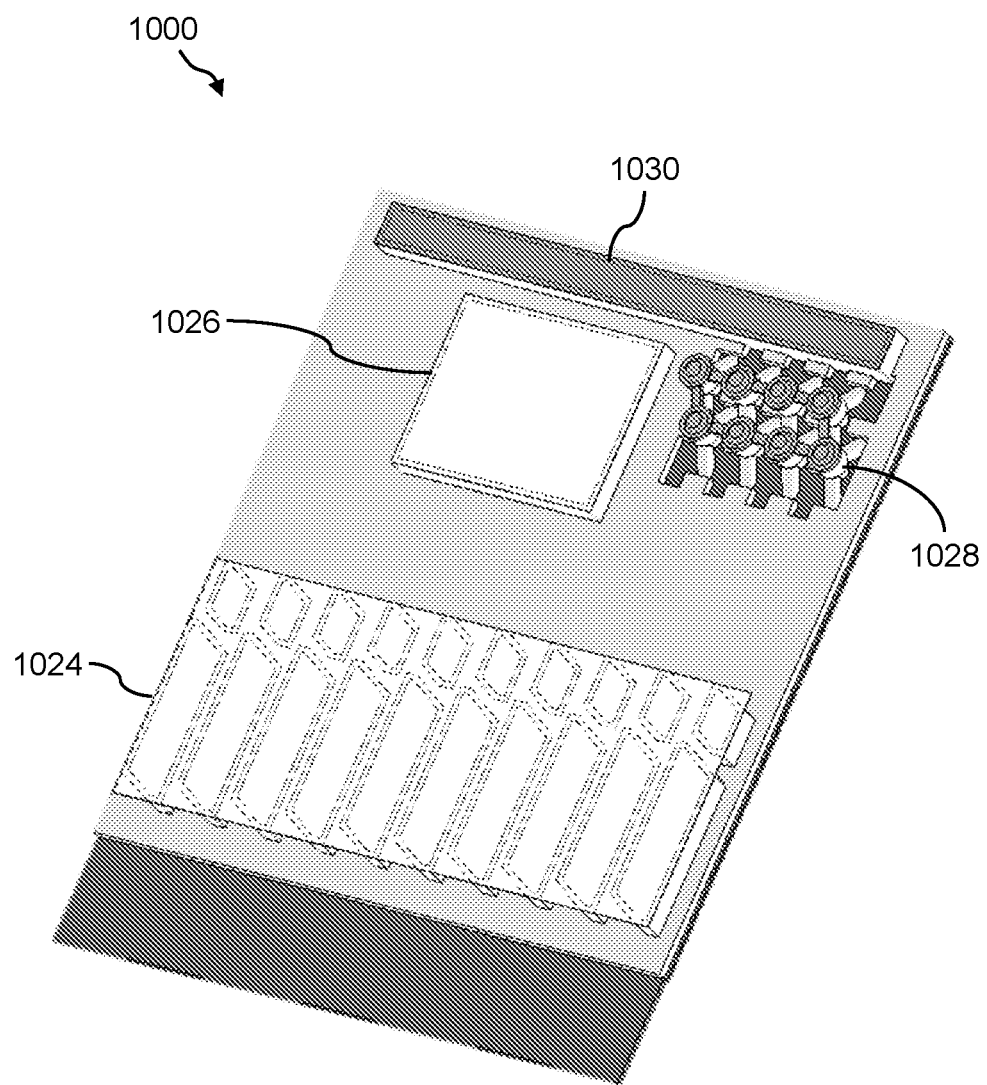
FIG. 12 illustrates a perspective back view of the fluidics cartridge shown in FIGS. 10 and 11.

FIGS. 10 and 11 illustrate a front view and a back view, respectively, of a fluidics cartridge 1000, which is another example of the presently disclosed fluidics cartridge that can be used in the vertical or substantially vertical position. FIG. 12 shows another view (a perspective back view) of fluidics cartridge 1000 shown in FIGS. 10 and 11. Fluidics cartridge 1000 comprises a front substrate, a back substrate, and a reservoir assembly similar to those described with reference to fluidics cartridge 300 of FIG. 3.

Referring now to FIG. 10, fluidics cartridge 1000 comprises a sample loading region 1010, a reagent dispense region 1012, a PCR region 1014, a waste collection region 1016, a detection region 1018, and a venting region 1020. Further, an electrode arrangement 1022 of droplet operations electrodes is provided for fluidly connecting the various regions. FIG. 10 also shows a set of electrical interconnects 1005 for supporting power and signals to fluidics cartridge 1000.

Referring now to FIGS. 11 and 12, a set of reagent reservoirs 1024 (i.e., off-cartridge reservoirs) are provided to support reagent dispense region 1012. A waste reservoir 1026 (i.e., off-cartridge reservoir) is provided to support waste collection region 1016. A set of sample loading ports 1028 is provided to support sample loading region 1010. Not shown is, for example, a CMOS detector for supporting detection region 1018. A vent port 1030 is provided to support venting region 1020.

Figure 15:
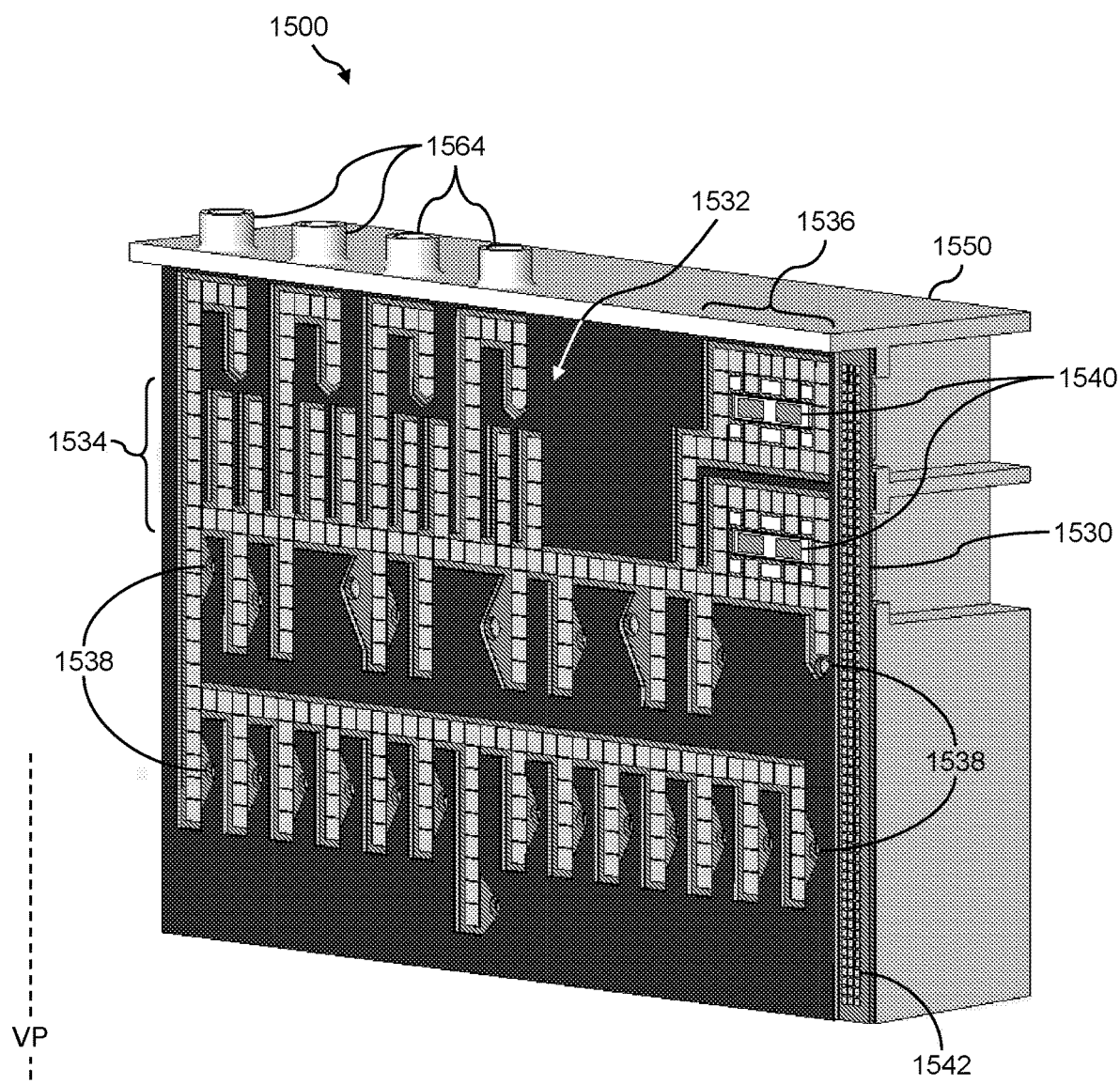
FIGS. 15 and 16 illustrate a front perspective view and a back perspective view, respectively, of yet another example of the presently disclosed fluidics cartridge that can be used in the vertical or substantially vertical position, wherein the loading ports are located at the top edge thereof.
Figure 16:
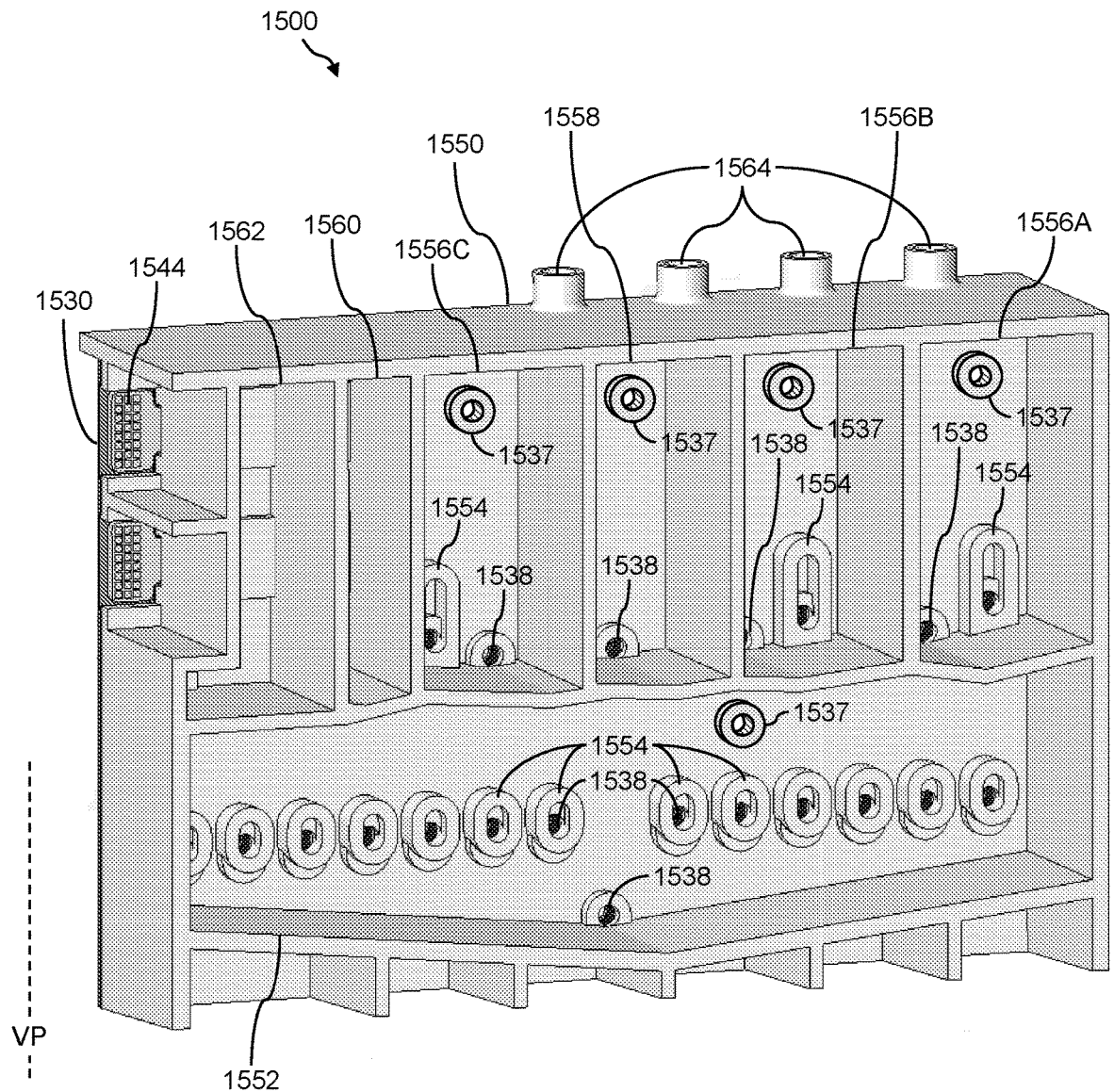

FIGS. 15 and 16 illustrate a front perspective view and a back perspective view, respectively, of a portion of a fluidics cartridge 1500, which is yet another example of the presently disclosed fluidics cartridge that can be used in the vertical or substantially vertical position, or at an angle ranging from vertical (90 degrees) to greater than 0 degrees, or at an angle ranging from vertical (90 degrees) to about 45 degrees.

Fluidics cartridge 1500 includes examples of certain other features that may be built into the presently disclosed fluidics cartridge that can be used in the vertical or substantially vertical position. For example, fluidics cartridge 1500 includes (1) an example of sample loading ports located at the top edge of the reservoir assembly, (2) an example of a library preparation region, (3) an example of a detection region for sequencing that is located near the edge of the fluidics cartridge, (4) an example of a large-volume reservoir, and (5) an example of a space saving technique of placing small reservoirs inside of larger reservoirs.

Fluidics cartridge 1500 comprises a back substrate 1530 (e.g., a PCB) and a reservoir assembly 1550 that are arranged together as shown. In FIGS. 15 and 16, fluidics cartridge 1500 is shown absent the front substrate. However, those skilled in the art will recognize that fluidics cartridge 1500 also includes a front substrate (not shown), wherein the front substrate and back substrate 1530 are separated by a droplet operations gap (not shown).

Referring now to FIG. 15, an electrode arrangement 1532 is provided on back substrate 1530. Electrode arrangement 1532 is designed to support droplet operations between various portions of fluidics cartridge 1500. Namely, fluidics cartridge 1500 includes a library preparation region 1534 and a detection region 1536. Electrode arrangement 1532 also includes lines or paths of droplet operations electrodes that surround library preparation region 1534 and detection region 1536 for supplying droplets from various reservoirs of reservoir assembly 1550. A plurality of upper flow paths 1537 and lower flow paths 1538 are provided in back substrate 1530 and reservoir assembly 1550 that are associated with the various reservoirs of reservoir assembly 1550. Further, a plurality of CMOS detectors 1540 are provided in detection region 1536 on back substrate 1530. Additionally, back substrate 1530 includes a set of electrical interconnects 1542, which supports power and signals to fluidics cartridge 1500.

Detection region 1536 and CMOS detectors 1540 can be used for sequencing operations. Detection region 1536 and CMOS detectors 1540 are located at a top corner edge of fluidics cartridge 1500. In some embodiments, it may be preferable to place the detectors near the edge of the fluidics cartridge to minimize the length of electrical traces from the CMOS daughterboard to the edge of the fluidics cartridge.

Figure 31:
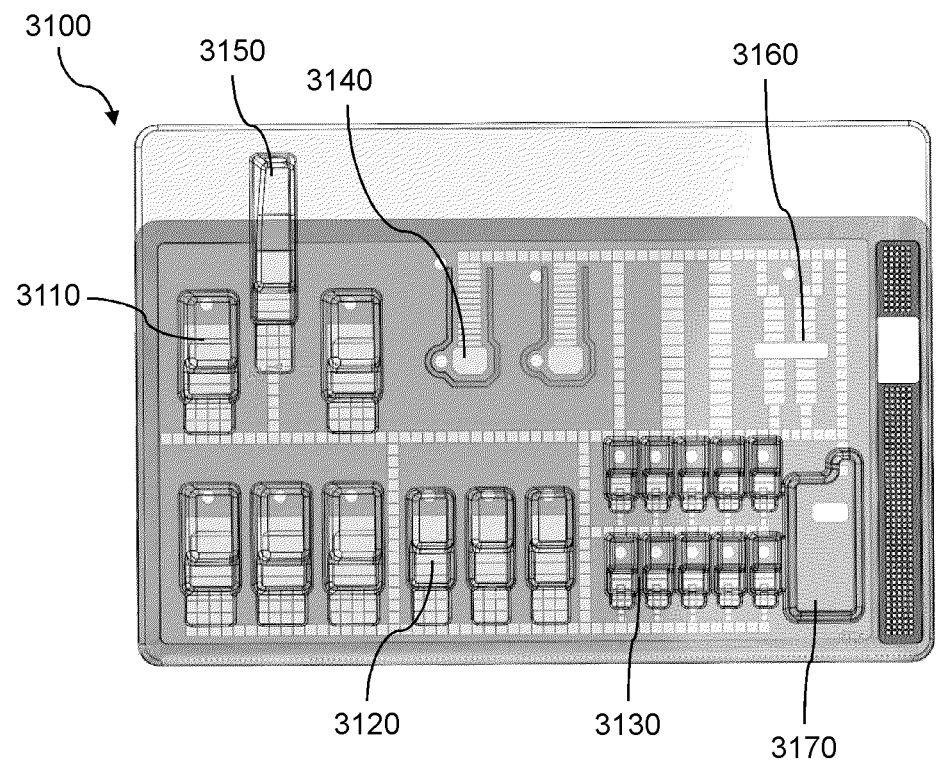
FIG. 31 illustrates an exemplary fluidics cartridge including both downward dispensing volumes and U-features for upward dispensing, wherein the electrowetting array is divided into multiple regions that perform different functions.

FIG. 31 shows an illustrative fluidics cartridge 3100 which comprises both downward dispensing volumes 3110, 3120 and 3130 of various sizes and U-features 3140 for upward dispensing. Some downward dispensing volumes may be connected to a sample loading port 3150. A U-feature 3170 may also be included for waste collection. An electrowetting array comprised of electrodes connects the different downward dispensing volumes and U-features and transports droplets to conduct reactions, such as clustering, primer extension, SBS, etc. The structural features and electrodes for certain reactions may be clustered on the fluidics cartridge into various functional regions. In some embodiments, a detection region may be included, which comprises a CMOS detector 3160.

Reservoir Assembly

Reservoirs may be affixed to either the front substrate or the back substrate, directly or indirectly. Reservoirs may have a variety of sizes to suite their purposes, such as holding a sample, a reagent, a buffer, a waste, an immiscible liquid, etc. For example, a reservoir may have a volume that is, is about, is more than, is less than, 1 mL, 2 mL, 3 mL, 4 mL, 5 mL, 6 mL, 7 mL, 8 mL, 9 mL, 10 mL, 20 mL, 30 mL, 40 mL, 50 mL, 60 mL, 70 mL, 80 mL, 90 mL, 100 mL, or a range between any two of the above-mentioned values. In some embodiments, the presently disclosed fluidics cartridge that can be used in the vertical or substantially vertical position comprises one or more small reservoirs inside a larger reservoir, which is a space-saving configuration of reservoirs. A reservoir may have any suitable shape, such as a U-cup shape, a trapezoidal shape, etc. In some embodiments, the reservoir may have a shape corresponding to the shape of the U-feature it is in fluidic communications with. In some embodiments, the reservoir may have an irregular shape to minimize dead volume.

As shown in FIGS. 6A and 6B, reservoir assembly 350 comprises a plate 352 that is designed to be fitted against the outside surface of back substrate 330. A set of reservoirs are integrated into plate 352 of reservoir assembly 350, wherein plate 352 and the reservoirs can be formed, for example, of molded plastic or glass. In one example, reservoir assembly 350 includes an oil reservoir 354 located in an upper region of fluidics cartridge 300, four reagent reservoirs 356 (e.g., reagent reservoirs 356A, 356B, 356C, 356D) located in a central region of fluidics cartridge 300, and a waste reservoir 358 located in a lower region of fluidics cartridge 300. In one example, the position of reagent reservoirs 356A, 356B, 356C, 356D can correlate to a polymerase chain reaction (PCR) region and detection region of fluidics cartridge 300.

In this example, oil reservoir 354, the four reagent reservoirs 356, and waste reservoir 358 are off-cartridge reservoirs. Off-cartridge reservoirs are reservoirs on fluidics cartridge 300 that are outside the droplet operations gap 312 and not in contact with the droplet operations surface. Droplet operations are conducted atop droplet operations electrodes 334 on a droplet operations surface. For example, in fluidics cartridge 300, droplet operations are conducted along the vertical plane VP in droplet operations gap 312.

Each of oil reservoir 354, the four reagent reservoirs 356, and waste reservoir 358 is in fluid communication with an opening or flow path arranged for flowing liquid from the off-cartridge reservoir into droplet operations gap 312. For example, each of oil reservoir 354, the four reagent reservoirs 356, and waste reservoir 358 has an upper flow path 336 and a lower flow path 338. Each of the upper flow paths 336 and lower flow paths 338 is an opening or through-hole that extends through both plate 352 of reservoir assembly 350 and back substrate 330.

FIGS. 3A and 3B shows, for example, each of the reagent reservoirs 356A, 356B, 356C, 356D and each of the corresponding reagent U-features 318A, 318B, 318C, 318D partially filled with a volume of reagent 362. Waste U-feature 320 and waste reservoir 358 is shown partially filled with a volume of waste liquid 364. The remaining volume in reagent reservoirs 356A, 356B, 356C, 356D; reagent U-features 318A, 318B, 318C, 318D; waste U-feature 320; waste reservoir 358; and droplet operations gap 312 is filled with a volume of filler fluid 360, wherein filler fluid 360 is supplied from oil reservoir 354.

The top end of fluidics cartridge 300 is vented to atmosphere. Because the top end of fluidics cartridge 300 is vented to atmosphere, air bubbles naturally tend to float to the top of fluidics cartridge 300 and exit to atmosphere. This feature of fluidics cartridge 300 provides benefit over conventional horizontally-mounted fluidics cartridges in which the presence and elimination of air bubbles can be problematic.

Referring now to FIG. 16, reservoir assembly 1550 includes a variety of various sized off-cartridge reservoirs. For example, reservoir assembly 1550 includes a large-volume reservoir 1552 that is located in the lower portion of reservoir assembly 1550. In sequencing by synthesis (SBS) applications, large volumes of reagents or buffers (e.g., 50-80 ml) can be preferred. Large-volume reservoir 1552 is designed to handle this large volume. Located near the bottom of large-volume reservoir 1552 is a lower flow path 1538 to the droplet operations gap. In fluidics cartridge 1500, large-volume reservoir 1552 can be, for example, a buffer reservoir.

A plurality of small reagent reservoirs 1554 are provided inside of large-volume reservoir 1552. In one example, thirteen reagent reservoirs 1554 are provided inside of large-volume reservoir 1552. The plurality of small reagent reservoirs 1554 inside of large-volume reservoir 1552 is an example of a space saving technique in fluidics cartridge 1500. Each of the reagent reservoirs 1554 is fluidly sealed from large-volume reservoir 1552 so that there is no liquid exchange between the reagent reservoirs 1554 and large-volume reservoir 1552. Reagent reservoirs 1554 can be sealed, for example, using plastic or foil. Associated with each of the reagent reservoirs 1554 is a lower flow path 1538 to the droplet operations gap. Examples of ways to implement reagent reservoirs 1554 are shown and described hereinbelow with reference to FIGS. 18, 19, 20, 21, 22, 23, 24, and 25.

Additionally, the upper portion of reservoir assembly 1550 includes a set of semi-large reservoirs. For example, reservoir assembly 1550 includes three semi-large reservoirs 1556 (e.g., semi-large reservoirs 1556A, 1556B, 1556C), as well as a semi-large reservoir 1558. Each of the semi-large reservoirs 1556 and the semi-large reservoir 1558 has a lower flow path 1538. Additionally, inside each of the three semi-large reservoirs 1556 is a small reagent reservoir 1554. In one example, the three semi-large reservoirs 1556 are reservoirs for holding SBS reagents. In one example, semi-large reservoir 1558 is used for holding additional reagents, which may include SBS reagents, clustering and paired end reagents, among others.

Whereas FIGS. 15 and 16 show only a portion of fluidics cartridge 1500, it can be assumed that fluidics cartridge 1500 comprises an oil reservoir, which is not shown. Accordingly, upper flow paths 1537 and lower flow paths 1538 are provided to accommodate the aqueous/oil exchange process in the off-cartridge reservoirs of fluidics cartridge 1500.

Additionally, the upper portion of reservoir assembly 1550 includes a compartment 1560 and a compartment 1562. Compartments 1560 and 1562 provide access for thermal control to detection region 1536 and CMOS detectors 1540.

Further, a set of loading ports 1564 is provided at the top edge of reservoir assembly 1550. Because loading ports 1564 are at the top edge of reservoir assembly 1550, they are easily accessible when fluidics cartridge 1500 is installed in an instrument. Loading ports 1564 can be used for loading any type of liquid directly into, for example, semi-large reservoirs 1556A, 1556B, and 1556C and semi-large reservoir 1558. In addition to space savings, another advantage of the configuration of a small reservoir inside of a larger reservoir is that while the small reservoir must be protected from liquid exchange, it is automatically protected from air exchange. Further, small volumes of reagents sometimes have to be stored for many months. However, currently small volumes of reagents that are stored for long periods of time sometimes evaporate away. The presently disclosed configuration of a small reservoir inside of a larger reservoir may help ensure that small volumes of reagents can be stored for long periods of time without evaporating away.

Figure 18:
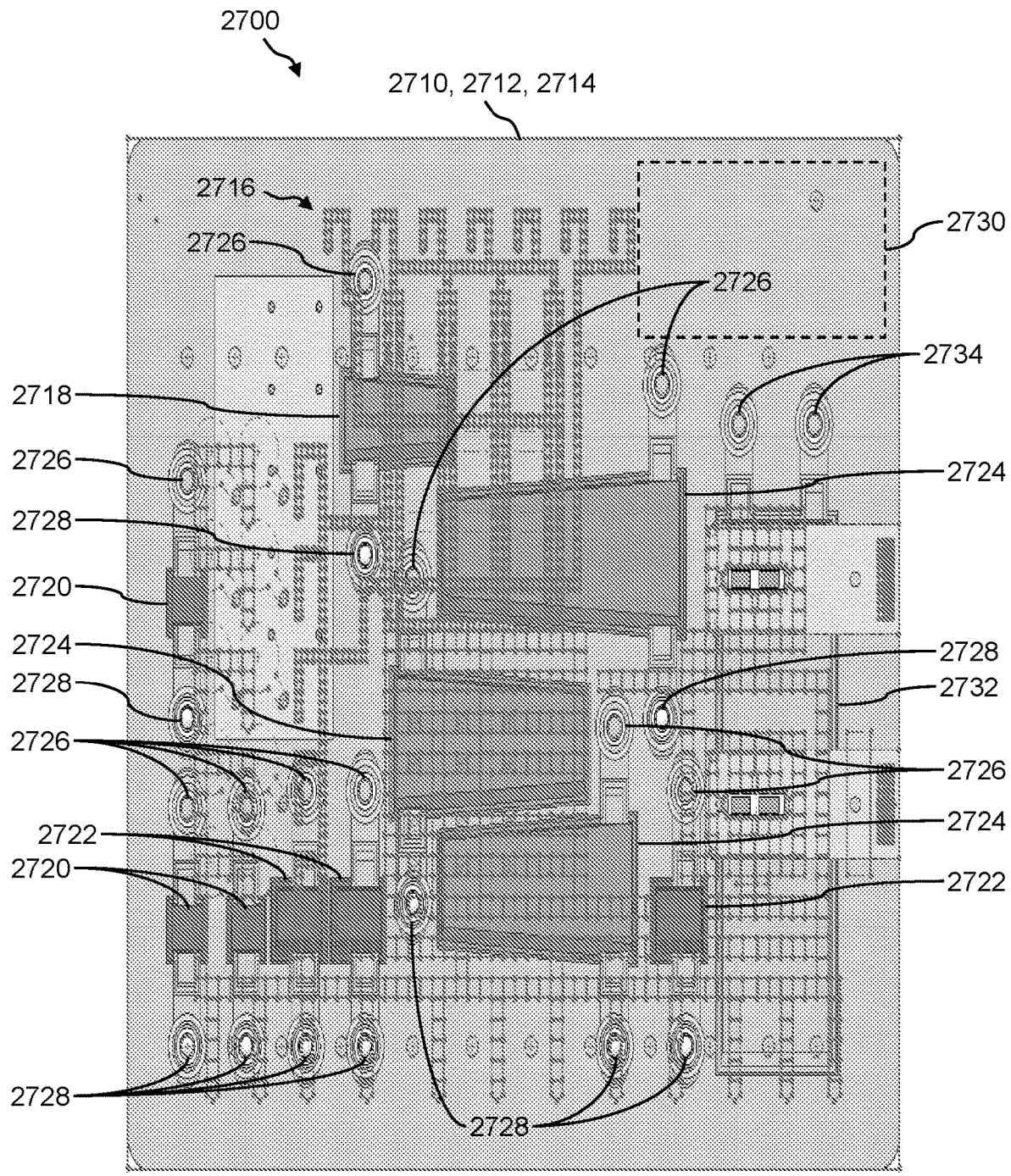
FIG. 18 illustrates a front plan view of yet another example of the presently disclosed fluidics cartridge that can be used in the vertical or substantially vertical position.
Figure 19:
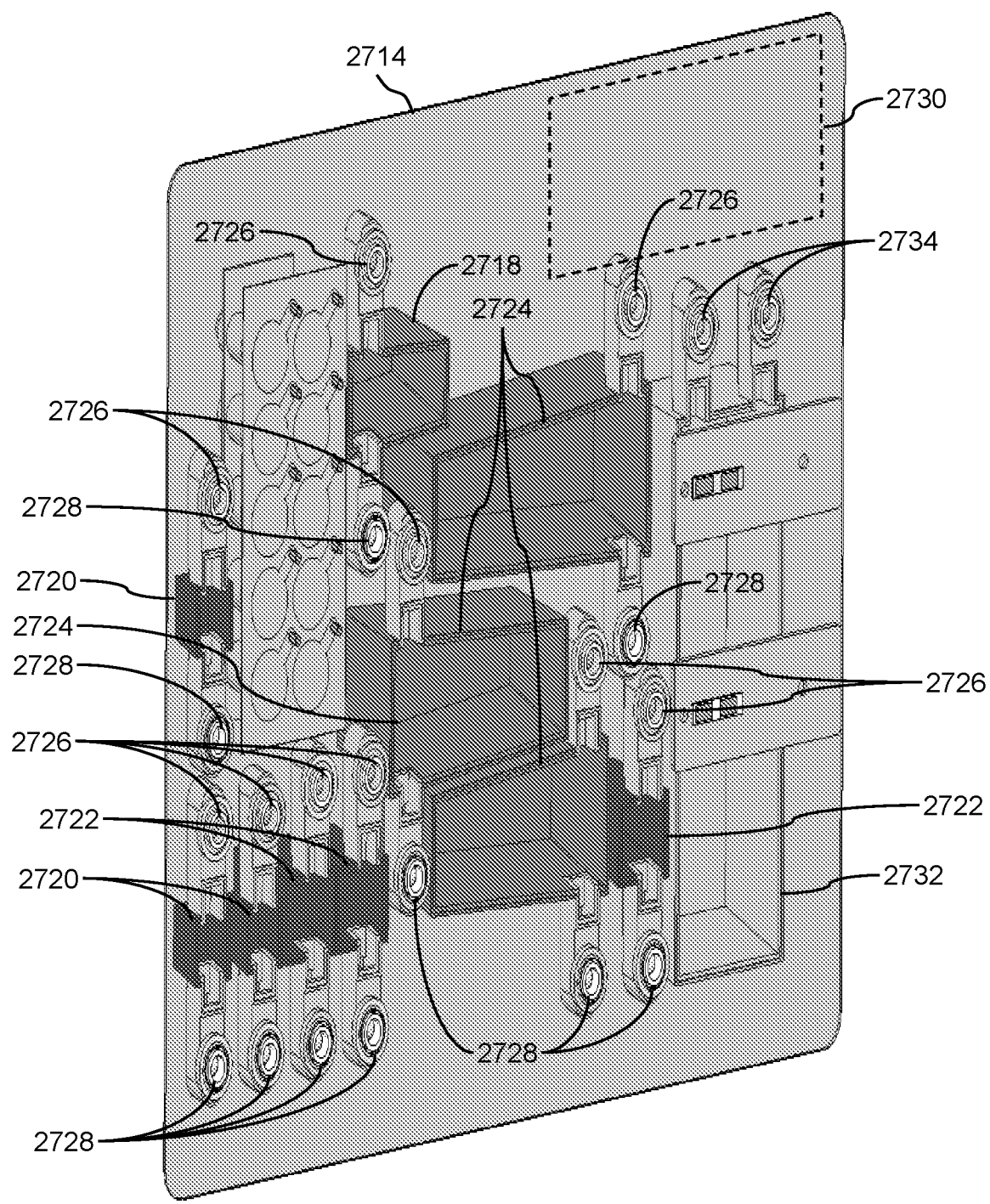
FIG. 19 illustrates a front perspective view of the reservoir assembly of the fluidics cartridge of FIG. 18.

FIG. 18 illustrates a front plan view of a fluidics cartridge 2700, while FIG. 19 illustrates a front perspective view of the reservoir assembly of fluidics cartridge 2700. Fluidics cartridge 2700 is yet another example of the presently disclosed fluidics cartridge that can be used in the vertical or substantially vertical position, or at an angle ranging from vertical (90 degrees) to greater than 0 degrees, or at an angle ranging from vertical (90 degrees) to about 45 degrees.

Referring now to FIGS. 18 and 19, fluidics cartridge 2700 comprises a front substrate 2710, a back substrate 2712 (e.g., a PCB), and a reservoir assembly 2714 that are arranged together as shown), wherein front substrate 2710 and back substrate 2712 are separated by a droplet operations gap (not shown). Further, an electrode arrangement 2716 is provided on back substrate 2712.

Fluidics cartridge 2700, and more particularly reservoir assembly 2714, includes a variety of various sized off-cartridge reservoirs. For example, reservoir assembly 2714 includes a 6,000-µl reservoir 2718, three 1,000-µl reservoirs 2720, three 3,000-µl reservoirs 2722, and three 65,000-µl reservoirs 2724. Each of the off-cartridge reservoirs has an upper flow path 2726 and a lower flow path 2728. Fluidics cartridge 2700 also includes an oil reservoir and input area 2730, albeit the off-cartridge oil reservoir and inputs are not shown. Additionally, reservoir assembly 2714 includes a 50-ml waste reservoir 2732 that has two flow paths 2734.

Passive Refill

In some embodiments, a reagent is loaded into the droplet operations gap without using an active pump, for example, through passive refill by hydraulic and capillary pressure inside the immiscible liquid. To achieve passive refill, the fluidics cartridges as disclosed herein may include a variety of design features to the droplet operations gap, the reservoir, or a combination thereof.

Figure 26:
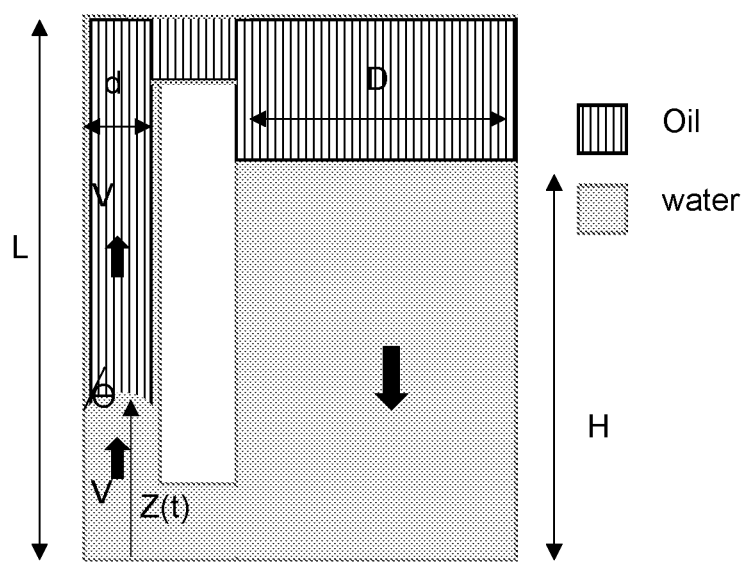
FIG. 26 illustrates the parameters of the fluidics cartridge to calculate the flow velocity for passive refill.

As shown in FIG. 26, the driven pressure (P) by gravity (g) and capillary force can be calculated by the formula below:

$$P = \Delta \rho g(H - Z(t)) + \frac{2 \Upsilon \cos \theta}{d}$$

wherein L: flow path length; H: initial water height; V: flow velocity; d: channel gap; Θ: contact angle; Y: surface tension; Δρ: Density mismatch; Z(t): liquid column height. Flow resistance by water may be calculated by the formula below:

$$\frac{\partial P}{\partial z} = \frac{-12\mu_w V}{d^2} \rightarrow P1 = \frac{-12\mu_w V}{d^2} Z(t)$$

and the resistance by oil may be calculated by the formula below:

$$\frac{\partial P}{\partial z} = \frac{-12\mu_o V}{d^2} \rightarrow P2 = \frac{-12\mu_o V}{d^2} (L - Z(t))$$

Therefore, the equilibration height may be calculated by the formula below:

$$H - Z(t) = \left(-\frac{\Upsilon(\cos\theta_1 + \cos\theta_2)}{d} + \frac{\Upsilon(\cos\theta_3 + \cos\theta_4)}{D}\right) / \Delta \rho g$$

and the flow velocity is:

$$V(t) = (H_S - Z(t))/T_0,$$

wherein time constant is:

$$T_0 = \frac{12\mu_o L}{\Delta \rho g d^2} = \left(\frac{12\mu_o L}{d^2}\right)\left(\frac{1}{\Delta \rho g}\right)$$

To keep enough flow rate for continuous droplet dispensing, i.e., V>1 mm/sec, extra pressure head is preferred ~V*T$_0$ (in current case ~7 mm). As shown above, flow resistance may be important for filling dynamics as any unexpected blocking of oil flow will significantly slow down the process and need extra pressure head for continuous droplet dispensing. In addition, oil properties are important for the flow resistance. Therefore, oil with low density and/or low viscosity is preferred. In order for faster refilling, the front side reservoir may be increased (bigger d) at the location of the flow path (see bulge 918 in FIG. 9).

Figure 27:
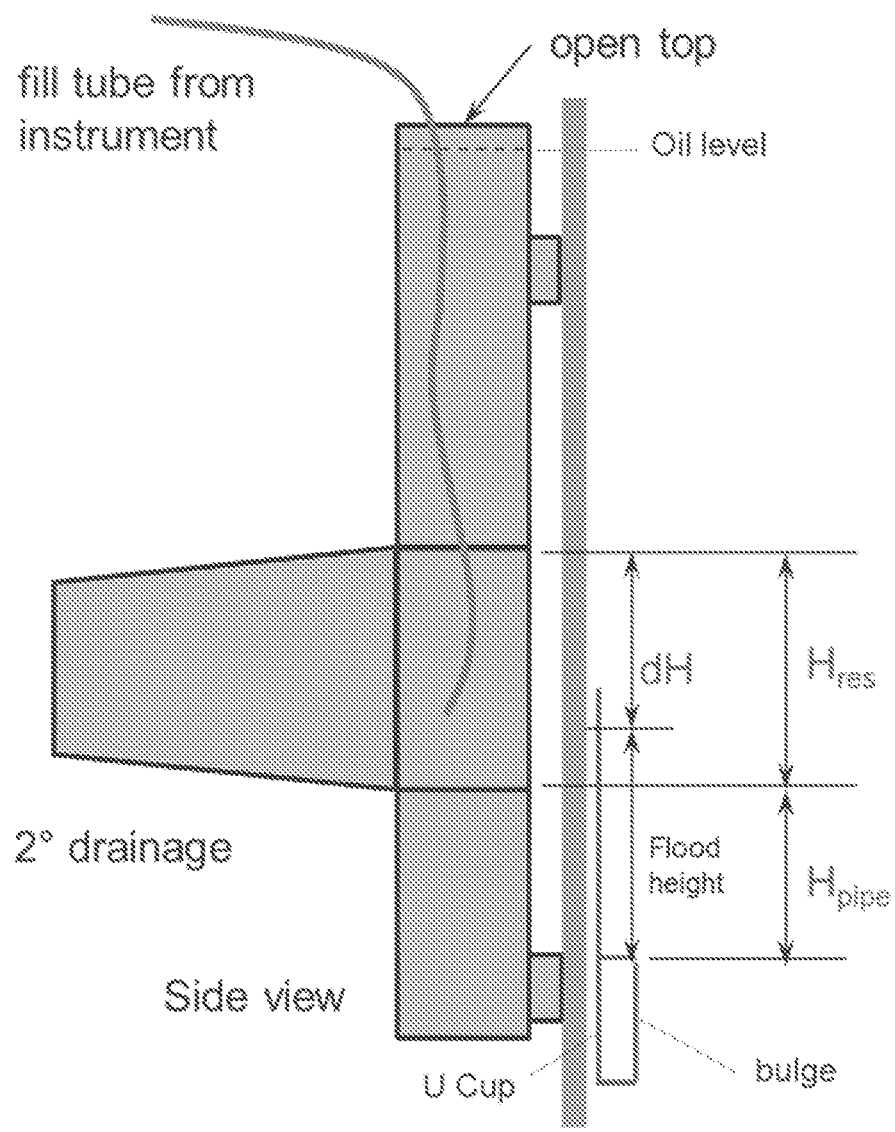
FIG. 27 illustrates the dispensing geometry for passive refill.

FIG. 27 shows a side view of an exemplary embodiment of a fluidics cartridge as disclosed herein where the reservoir has elongated top and bottom sections to minimize the amount of dead volume (H$_{pipe}$) and to maximize pressure head (H$_{res}$) for optimized passive refill.

Figure 20:
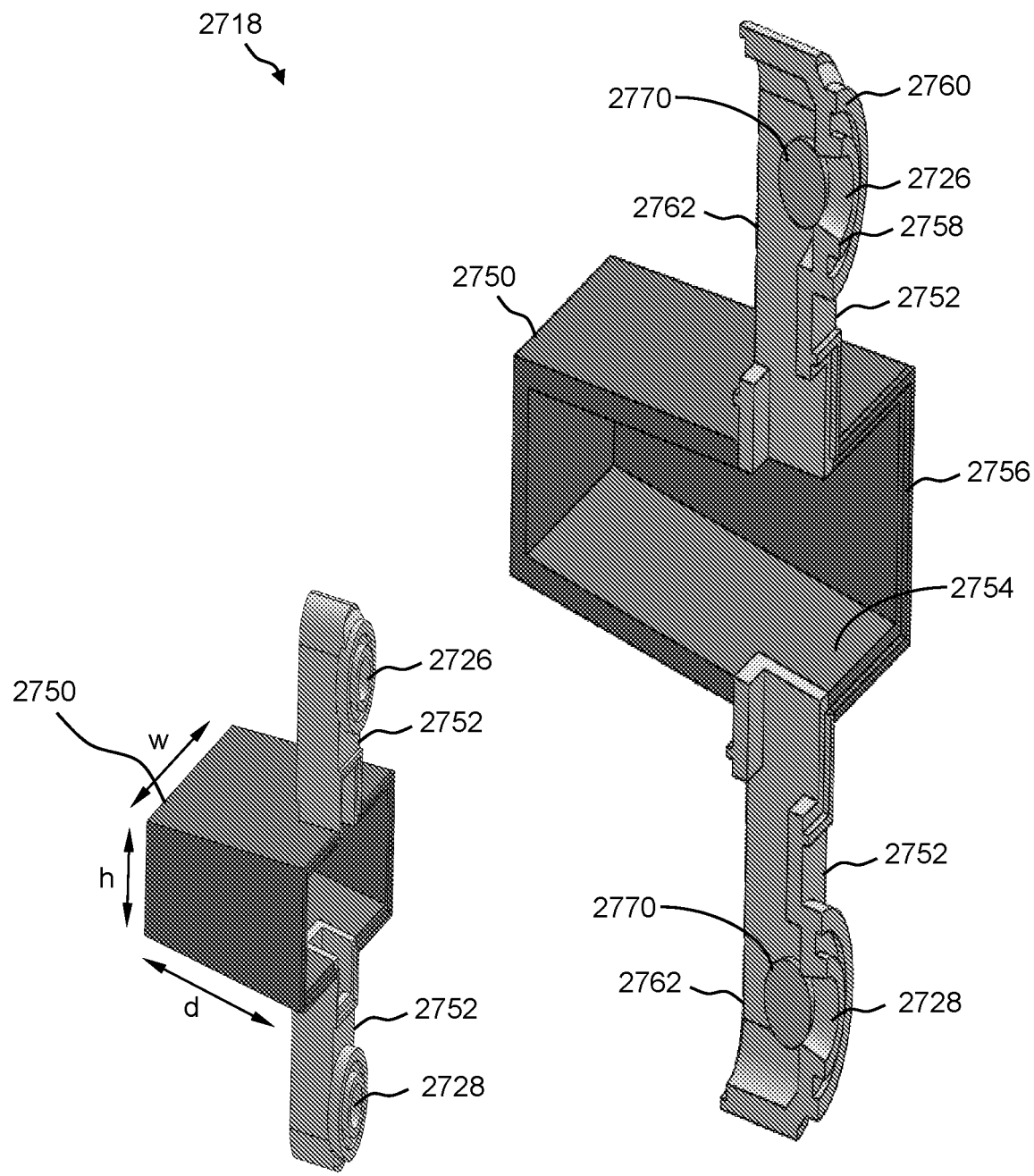
FIG. 20 shows a perspective view and a cross-sectional view of an example of a 6,000-μl reservoir of the fluidics cartridge of FIGS. 18 and 19 and also shows an example of a ball and wax seal.

FIG. 20 shows a perspective view and a cross-sectional view of an example of 6,000-μl reservoir 2718 of fluidics cartridge 2700 of FIGS. 18 and 19. The details shown in FIG. 20 of 6,000-μl reservoir 2718 are also generally applicable to the 1,000-μl reservoirs 2720, the 3,000-μl reservoirs 2722, and the 65,000-μl reservoirs 2724, albeit with different dimensions.

In this example, 6,000-μl reservoir 2718 includes a body 2750, which is the main fluid reservoir portion. In one example, body 2750 has a depth d of about 25 mm, a height h of about 10 mm, and a width w of about 28 mm. 6,000-μl reservoir 2718 also includes two extensions 2752 (an upper and lower) that provide flow paths from body 2750 to upper flow path 2726 and lower flow path 2728, respectively. Namely, upper flow path 2726 is integrated into the upper end of the upper extension 2752 and lower flow path 2728 is integrated into the lower end of the lower extension 2752. Each of the extensions 2752 can hold about 400 μl of liquid.

Additionally, body 2750 of 6,000-μl reservoir 2718 has a lower surface 2754 that has a draft (or slope) of about 5 degrees. A front foil seal raised ridge 2756 is provided around the edge of body 2750. An adhesive trace 2758 is provided around each of the upper flow path 2726 and lower flow path 2728. Further, a PCB port interface 2760 is provided around each of the upper flow path 2726 and lower flow path 2728. Further, a rear foil seal raised ridge 2762 is provided around the edge of both extensions 2752.

FIG. 20 also shows an example of using a ball and wax seal to control the flow of liquid through upper flow path 2726 and lower flow path 2728. For example, a ball 2770 is shown at the opening at each of the upper flow path 2726 and lower flow path 2728. Namely, one ball 2770 is used to seal the opening of upper flow path 2726. The other ball 2770 is used to seal the opening of lower flow path 2728. In one example, the balls 2770 are 4-mm diameter glass balls that are held in place by wax. Preferably, the wax is a low melting temperature wax that is compatible with the chemistry used in the fluidic cartridge. In some embodiments, the wax may include an alkane wax, paraffin, wafer bonding wax, docosane, tricosane, or bleached bees wax, among others. Upon melting the wax, ball 2770 drops by gravity, thereby opening the port to liquid flow.

Figure 21:
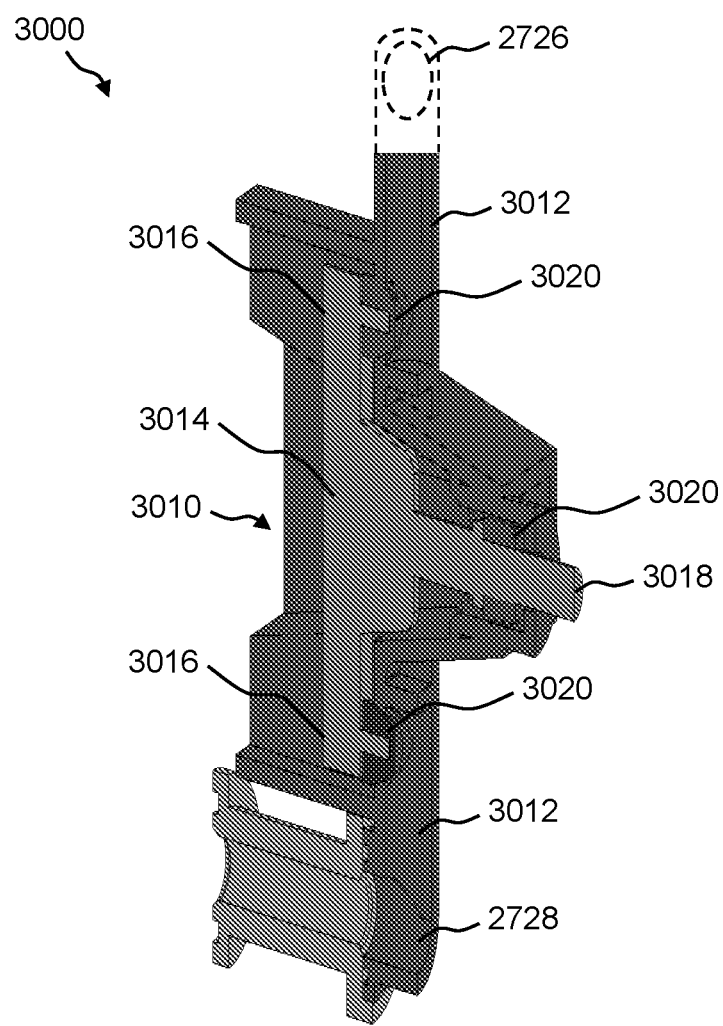
FIG. 21 shows a cross-sectional perspective view of an example of an off-cartridge reservoir that uses mechanical elastomers to control the flow of liquid therethrough.

FIG. 21 shows a cross-sectional perspective view of an example of an off-cartridge reservoir 3000 that uses mechanical elastomers to control the flow of liquid therethrough. In this example, off-cartridge reservoir 3000 includes a body 3010, which is the main fluid reservoir portion. Off-cartridge reservoir 3000 also includes two extensions 3012 (an upper and lower) that provide flow paths from body 3010 to upper flow path 2726 and lower flow path 2728, respectively. A valve member 3014 is provided inside body 3010. The shape and features of valve member 3014 are designed to fit in body 3010 and extensions 3012. Namely, valve member 3014 includes two arms 3016 and an actuator 3018. Three elastomers 3020 are provided with respect to valve member 3014. Namely, there is one elastomer 3020 at the end of the upper arm 3016 and in upper flow path 2726. There is another elastomer 3020 at the end of the lower arm 3016 and in lower flow path 2728. There is yet another elastomer 3020 at the tip of actuator 3018. Actuator 3018 is mechanically coupled to an external device by which valve member 3014 can be actuated to open and close upper flow path 2726 and lower flow path 2728 of off-cartridge reservoir 3000.

Figure 22:
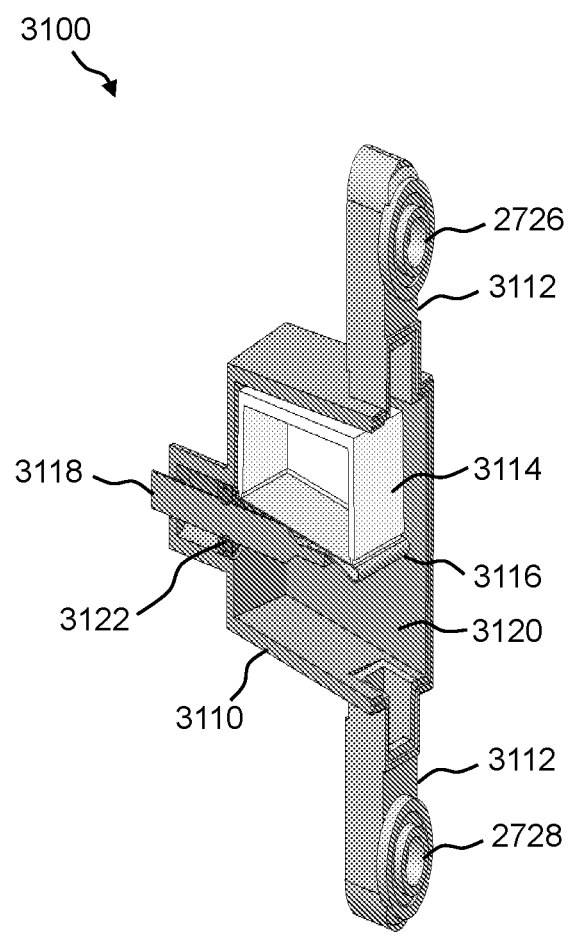
FIG. 22 shows a cross-sectional perspective view of an example of an off-cartridge reservoir that uses a replaceable foil-sealed reservoir inside a reservoir compartment.

FIG. 22 shows a cross-sectional perspective view of an example of an off-cartridge reservoir 3100 that uses a replaceable foil-sealed reservoir inside a reservoir compartment. In this example, off-cartridge reservoir 3100 includes a body 3110. Off-cartridge reservoir 3100 also includes two extensions 3112 (an upper and lower) that provide flow paths from body 3110 to upper flow path 2726 and lower flow path 2728, respectively. A portion of body 3110 is designed to receive a replaceable foil-sealed reservoir 3114. Replaceable foil-sealed reservoir 3114 included a foil seal 3116 for holding liquid therein. A pull-tab or piercer 3118 is provided for opening foil seal 3116 and releasing liquid into a secondary portion 3120 of body 3110. A seal 3122 is provided at pull-tab or piercer 3118 for preventing leakage.

Figure 23:
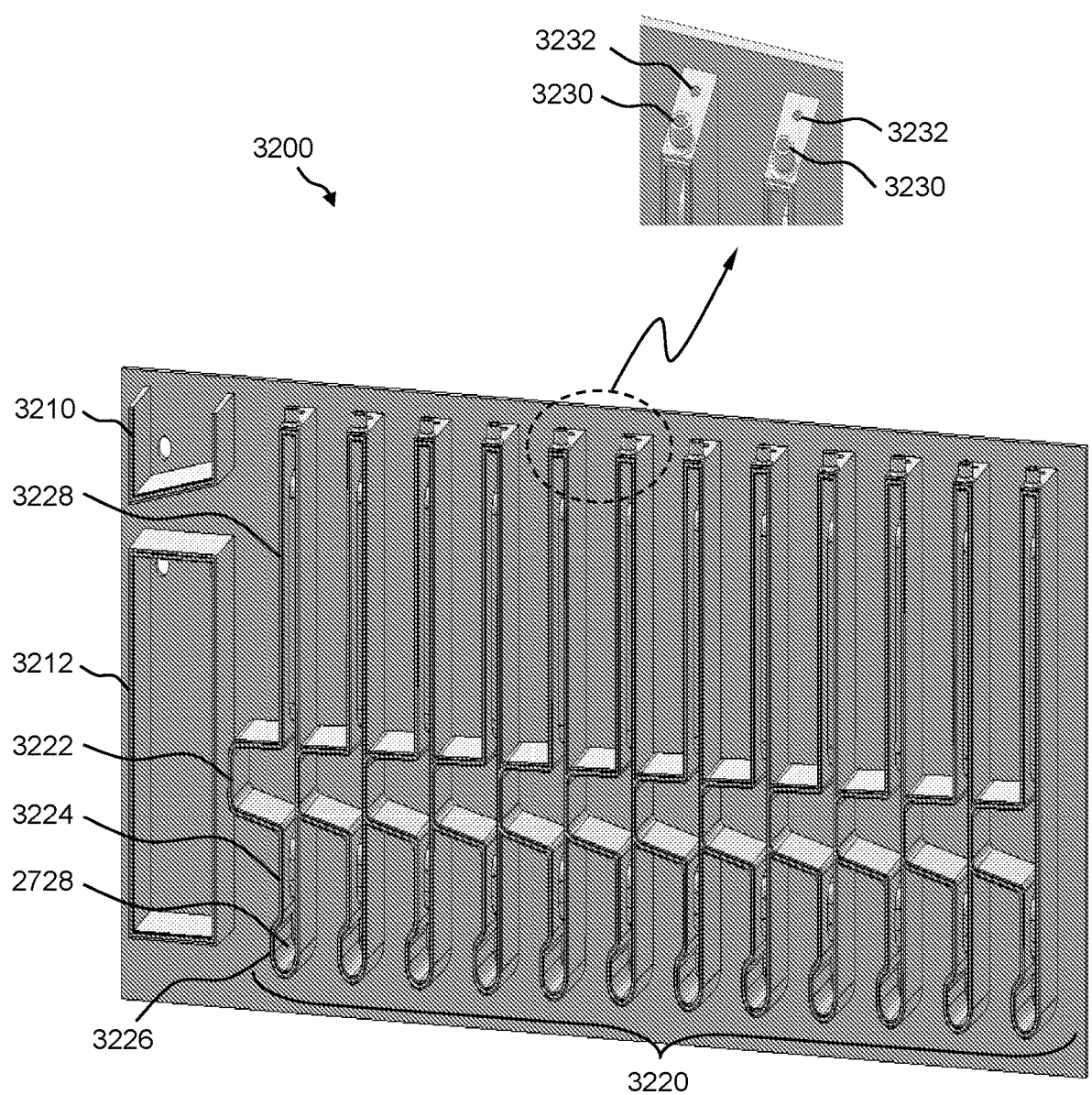
FIG. 23 shows a perspective view of an example of a portion of a reservoir assembly comprising elongated reservoirs that can be used with the presently disclosed fluidics cartridge that can be used in the vertical or substantially vertical position.

FIG. 23 shows a perspective view of an example of a portion of a reservoir assembly 3200 comprising elongated off-cartridge reservoirs that can be used with the presently disclosed fluidics cartridge that can be used in the vertical or substantially vertical position. In this example, reservoir assembly 3200 includes an oil reservoir 3210, a waste reservoir 3212, and a plurality of elongated reservoirs 3220. Oil reservoir 3210, waste reservoir 3212, and the plurality of elongated reservoirs 3220 are off-cartridge reservoirs.

Each of the elongated reservoirs 3220 includes a main storage portion 3222. A lower pipe 3224 extends downward from the lower portion of main storage portion 3222 to a lower flow path 2728. A bulge portion 3226 surrounds lower flow path 2728. An upper pipe 3228 extends upward from the upper portion of main storage portion 3222 to the upper flow path, which is implemented as a pump input port 3230 in the upper end of upper pipe 3228. A vent port 3232 is also provided in the upper end of upper pipe 3228, near pump input port 3230. A foil seal (not shown) is provided at the edge of each of the elongated reservoirs 3220. In one example, each of the elongated reservoirs 3220 can hold a volume of about 1.6 ml. Elongated reservoirs 3220 are designed to minimize the amount of dead volume. In one example, the dead volume in each of the elongated reservoirs 3220 is only about 0.5 ml.

Figure 24:
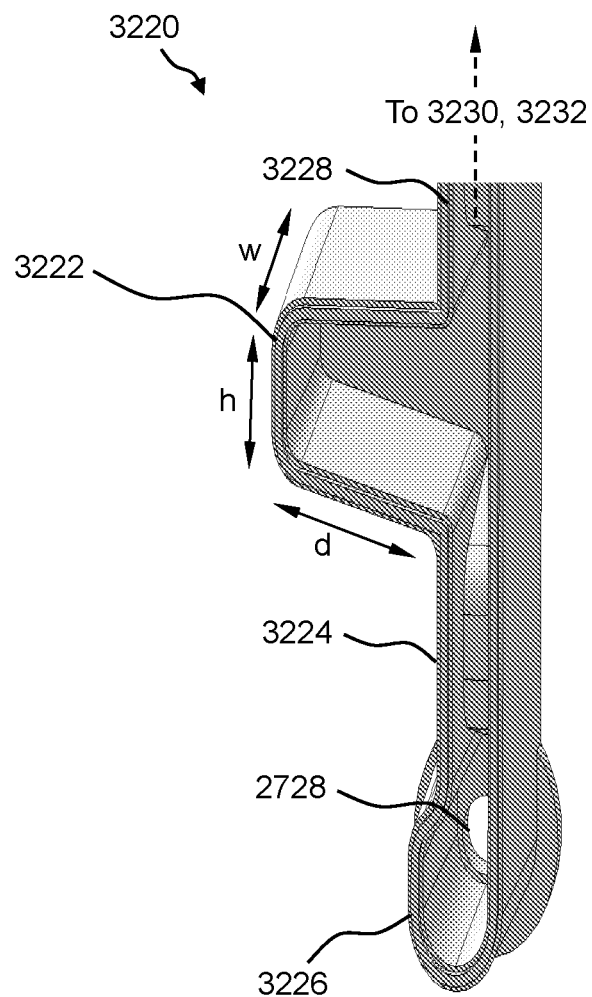
FIG. 24 shows a close up view of a portion of the elongated reservoir of the reservoir assembly of FIG. 23.

FIG. 24 shows a close up view of a portion of one elongated reservoir 3220 of reservoir assembly 3200 of FIG. 23. In this view, bulge portion 3226 can be seen more clearly surrounding lower flow path 2728. In one example, main storage portion 3222 has a depth d of about 13 mm, a width w of about 13 mm, and a height h of about 10 mm. In one example, the length of lower pipe 3224 is about 15 mm.

Flow Paths

The reservoirs disclosed herein are in fluidic connection with the droplet operations gap to provide the liquids needed for the droplet operations. In some embodiments, a reservoir is in fluid communication with the droplet operations gap through a flow path. In some embodiments, more than one flow paths are comprised in a reservoir, for example, a top flow path and a lower flow path. In some embodiments, the height of the droplet operations gap at the position of a flow path is greater than the height of the droplet operations gap.

Figure 8:
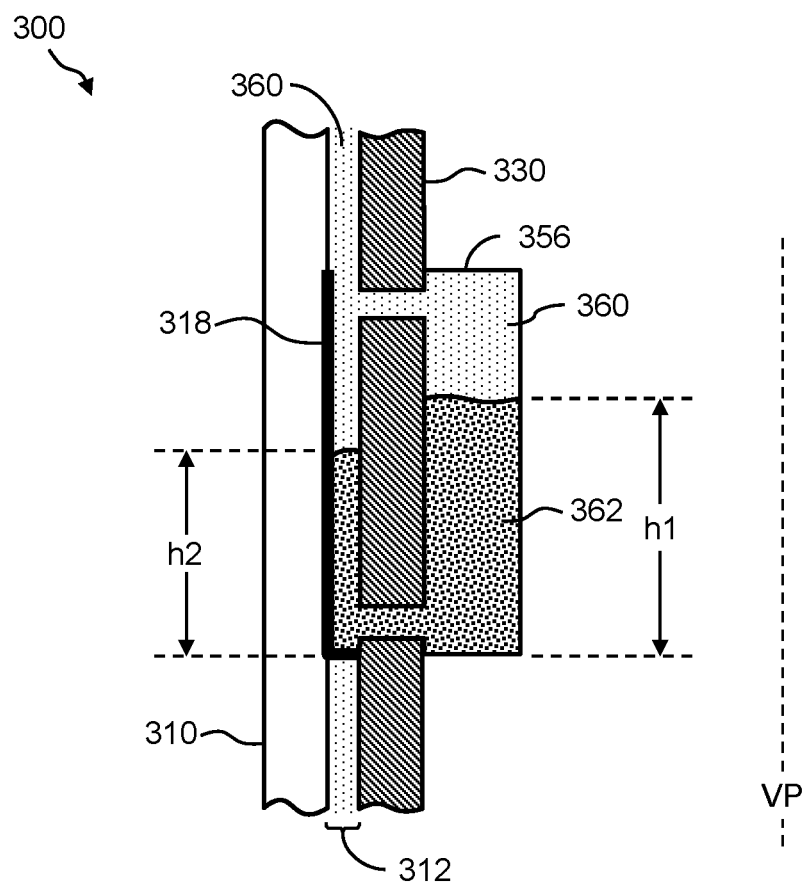
FIG. 8 illustrates a side view of an example of a reservoir portion of the presently disclosed fluidics cartridge that can be used in the vertical or substantially vertical position.

FIG. 8 illustrates a side view of an example of a reservoir portion of, for example, fluidics cartridge 300, which can be used in the vertical or substantially vertical position. FIG. 8 shows that the head height of reagent is different in the off-cartridge reservoir vs. in the U-feature in droplet operations gap. For example, FIG. 8 shows that reagent 362 in reagent reservoir 356 has a certain head height h1, while reagent 362 in reagent U-feature 318 has a certain head height h2, wherein the head height h1 in reagent reservoir 356 is greater than the head height h2 in reagent U-feature 318.

Figure 9A:
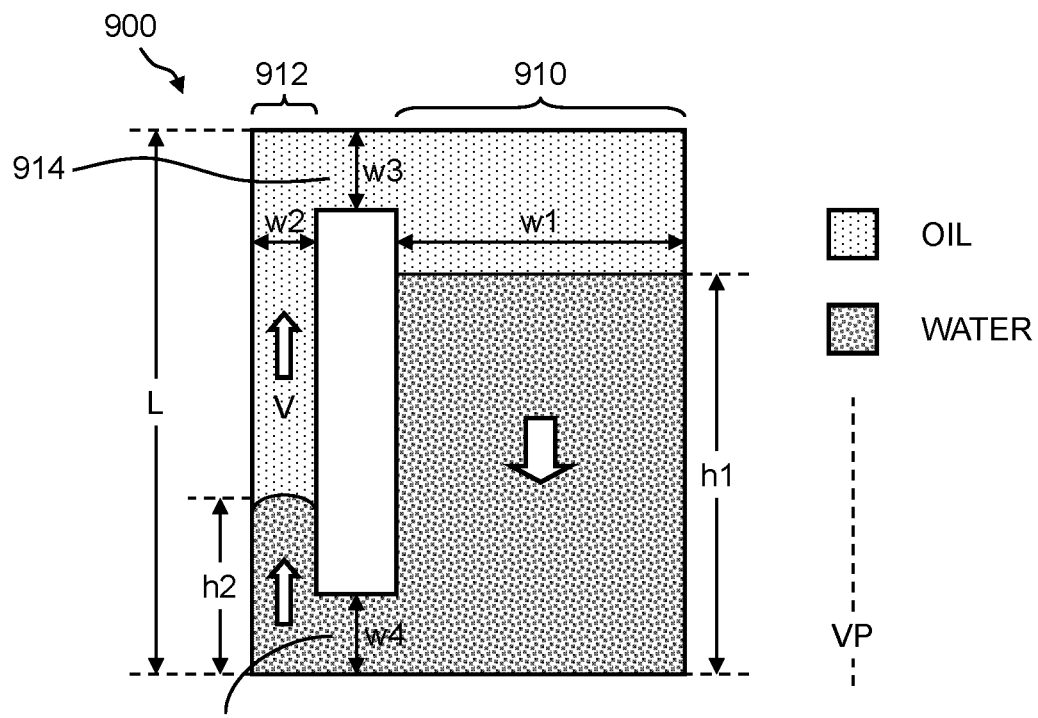
FIGS. 9A and 9B illustrate examples of the design parameters of the reservoirs for efficient aqueous/oil exchange on the presently disclosed fluidics cartridge.
Figure 9B:
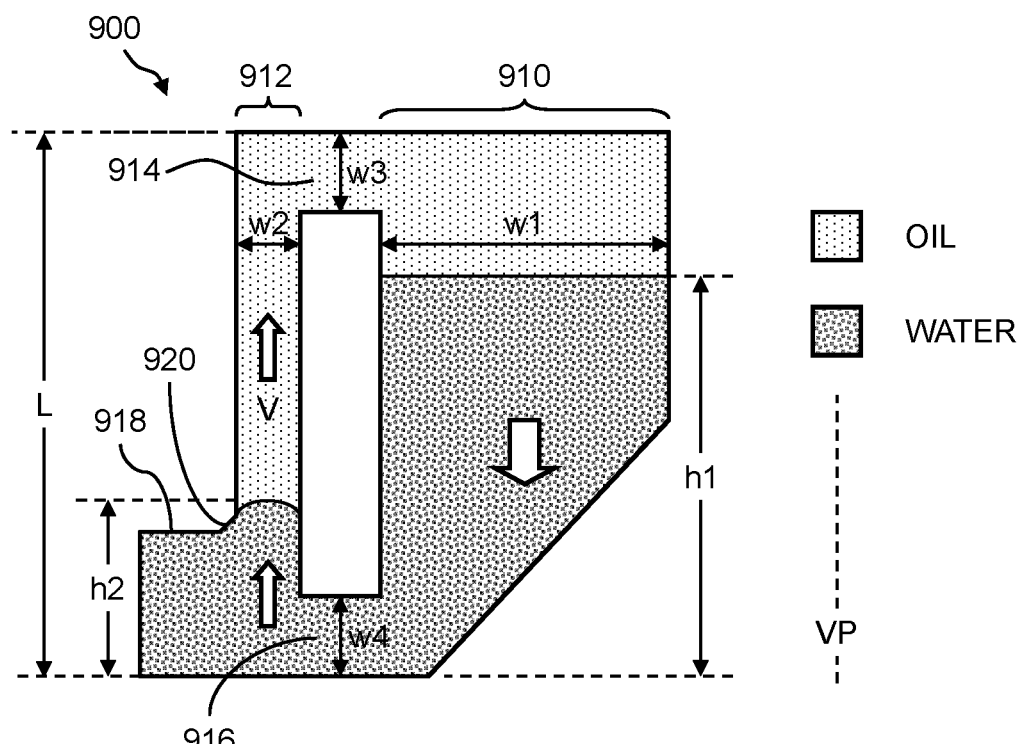

FIGS. 9A and 9B illustrate examples of the design parameters of the reservoirs for efficient aqueous/oil exchange on the presently disclosed fluidics cartridge. Namely, FIG. 9A shows a simplified geometry of a tank structure 900 that represents an off-cartridge reservoir with respect to the droplet operations gap in the presently disclosed fluidics cartridge. For example, tank structure 900 comprises a tank portion 910 and a channel portion 912, wherein channel portion 912 is oriented substantially along the vertical plane VP. Tank portion 910 and channel portion 912 are fluidly connected via an upper flow path 914 at the upper end of channel portion 912 and a lower flow path 916 at the lower end of channel portion 912.

In tank structure 900, tank portion 910 corresponds, for example, to reagent reservoir 356 of fluidics cartridge 300; channel portion 912 of tank structure 900 corresponds to droplet operations gap 312 of fluidics cartridge 300; upper flow path 914 corresponds to upper flow path 336 of reagent reservoir 356; and lower flow path 916 corresponds to lower flow path 338 of reagent reservoir 356.

Tank portion 910 of tank structure 900 has a width w1, channel portion 912 of tank structure 900 has a width w2, upper flow path 914 of tank structure 900 has a width w3, and lower flow path 916 of tank structure 900 has a width w4. FIG. 9A shows tank structure 900 partially filled with reagent 362, wherein reagent 362 is at the bottom of tank structure 900. The remaining volume of tank structure 900 is filled with filler fluid 360, wherein filler fluid 360 is at the top of tank structure 900.

As described in FIG. 8, reagent 362 in tank portion 910 of tank structure 900 has the head height h1, while reagent 362 in channel portion 912 of tank structure 900 has the head height h2, wherein the head height h1 in tank portion 910 is greater than the head height h2 in channel portion 912. A design feature of tank structure 900 is that widths w1, w2, w3, and w4 are set such that the head height h2 in channel portion 912 is held substantially constant even while the head height h1 in tank portion 910 is changing due to the depletion of reagent 362 in tank structure 900. Further, channel portion 912 of tank structure 900 has a flow path length L and the liquid inside tank structure 900 has a flow velocity V. The flow path length L can be, for example, longer than h1 and range from about 40 mm to about 100 mm. In some embodiments, h1-h2 is less than about 20 mm. Generally, the height of h1-h2 is driven by gravity and capillary forces.

Generally, the width w1 of tank portion 910 is significantly greater than the width w2 of channel portion 912. For example, the width w1 can be from about 10 mm to about 75 mm. The width w2 can be from about 0.4 mm to about 1.2 mm in one example, or from about 0.7 mm to about 1 mm in another example, or is about 0.8 mm in yet another example. So that the width w2 is the controlling parameter with respect to flow, it is preferable that both the width w3 of upper flow path 914 and the width w4 of lower flow path 916 are ≥width w2 of channel portion 912.

In tank structure 900, the filling of the reagent (e.g. reagent 362) into the filler fluid (e.g. filler fluid 360) is driven by capillary forces and gravity. This process is very sensitive to the difference in density between the reagent and the filler fluid. In some embodiments, these fluids may include silicone oil, hexadecane, or mineral oil.

Other features can be built into the off-cartridge reservoirs of the presently disclosed fluidics cartridge, as represented by tank structure 900 shown in FIG. 9B. In one example, the lower corner of tank portion 910 that is farthest from channel portion 912 can be beveled toward channel portion 912. This reduces or substantially eliminates the possibility of dead volume in side tank structure 900. Dead volume means any volume of liquid inside the fluidics cartridge that is trapped and cannot be delivered for use to any portion of the fluidics cartridge.

Additionally and still referring to FIG. 9B, to minimize the dependency of flowrate on the width w2 of channel portion 912, a bulge 918 can be built into the side of channel portion 912 opposite lower flow path 916. Bulge 918 can be any geometry, such as rectangular, square, circular, ovular, and the like. Bulge 918 helps to reduce or substantially eliminate the capillary effects in tank structure 900. In one example, the width w2 of channel portion 912 is about 1 mm and the width of bulge 918 is about 3 mm. Further, bulge 918 can include a tapered portion 920 that provides a transition from the 3 mm width to the channel portion 912.

Sample Loading Ports

Figure 13:
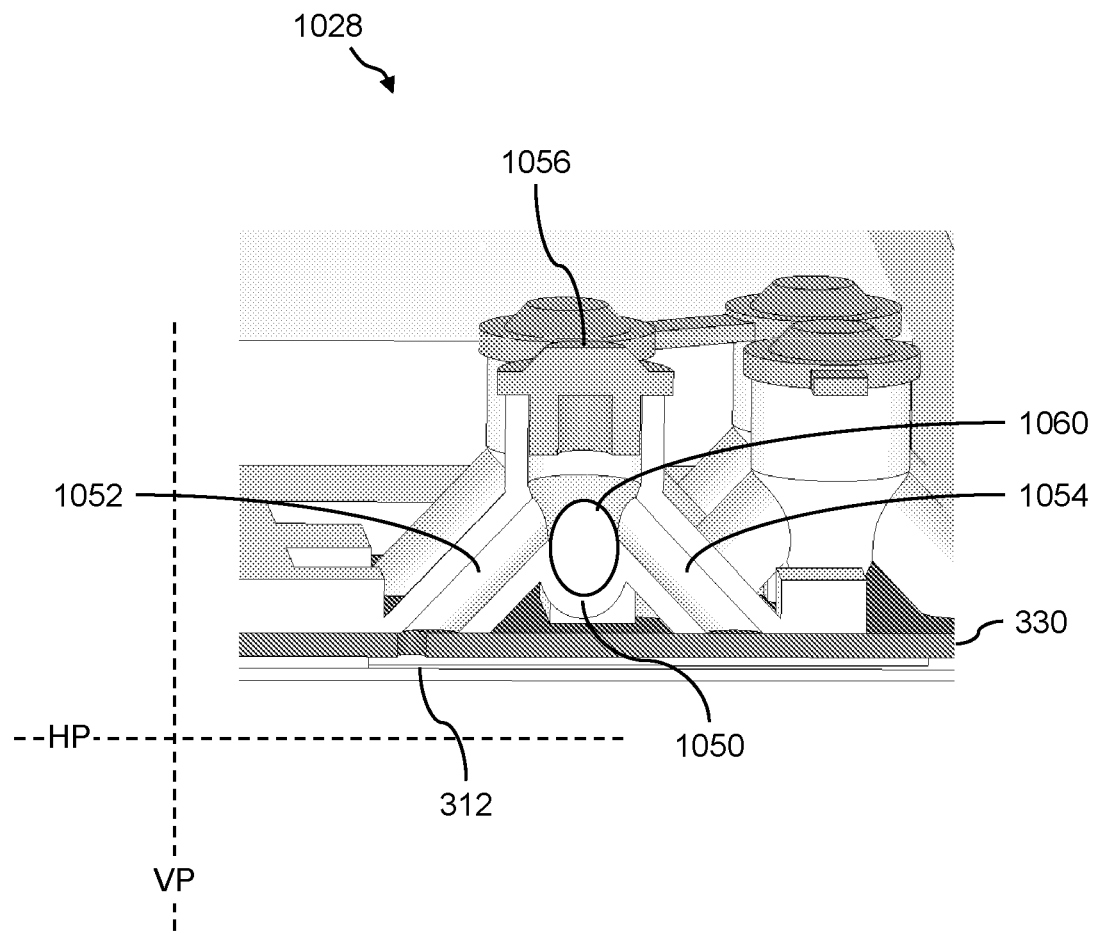
FIGS. 13 and 14 illustrate side views of an example of a sample loading port of the presently disclosed fluidics cartridge and a process of loading sample liquid into the fluidics cartridge.
Figure 14:
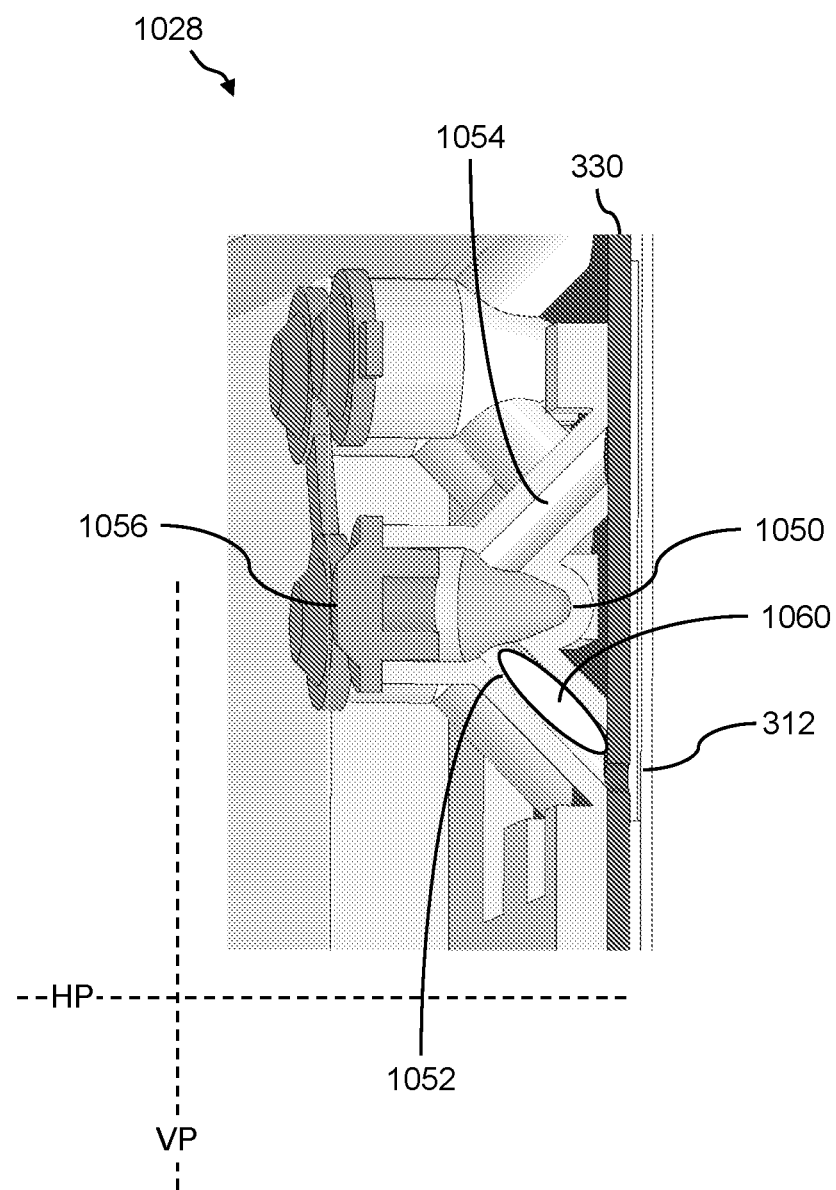

FIGS. 13 and 14 illustrate side views of an example of sample loading port 1028 of fluidics cartridge 1000 shown in FIGS. 10, 11, and 12 and a process of loading sample liquid into fluidics cartridge 1000. Sample loading port 1028 includes, for example, a storage chamber 1050, a flow channel 1052, and a flow channel 1054. Sample loading port 1028 also includes a cap 1056 for capping storage chamber 1050. Cap 1056 can be designed for easily snap-fitting onto storage chamber 1050.

The process of loading sample liquid into fluidics cartridge 1000 using sample loading port 1028 may include, but is not limited to, the following steps. This process provides a passive or semi-passive method of dispensing a sample liquid into the droplet operations gap.

At one step, the user holds fluidics cartridge 1000 in the horizontal position (i.e., along horizontal plane HP).

At another step, the user removes cap 1056 and pipettes a small volume of sample liquid 160 into storage chamber 1050 of sample loading port 1028.

At yet another step, the user replaces cap 1056 onto sample loading port 1028. At the completion of this step, sample loading port 1028 is capped and holding a small volume of sample liquid 160 in storage chamber 1050 as shown in FIG. 13.

At yet another step, the user flips fluidics cartridge 1000 into the vertical position (i.e., along vertical plane VP) and inserts fluidics cartridge 1000 into the instrument, such as into instrument 110 shown in FIG. 2A. In so doing, sample liquid 160 flows, for example, from storage chamber 1050 into flow channel 1052 of sample loading port 1028 as shown in FIG. 14.

At still another step, using the instrument and/or instrument deck (e.g., instrument 110 and/or instrument deck 115 of FIG. 2A), filler fluid is loaded into the droplet operations gap. In so doing, the filler fluid pushes sample liquid 160 out of flow channel 1052 of sample loading port 1028 and into the droplet operations gap. Namely, when the droplet operations gap is filled with filler fluid, the filler fluid comes in contact with the edge of sample liquid 160 in flow channel 1052 (i.e., the lower flow channel) and then pulls sample liquid 160 into the droplet operations gap. At the same time, filler fluid enters flow channel 1054 (i.e., the upper flow channel), which flushes sample liquid 160 out of flow channel 1052 (i.e., the lower flow channel) and into the droplet operations gap.

Figure 17A:
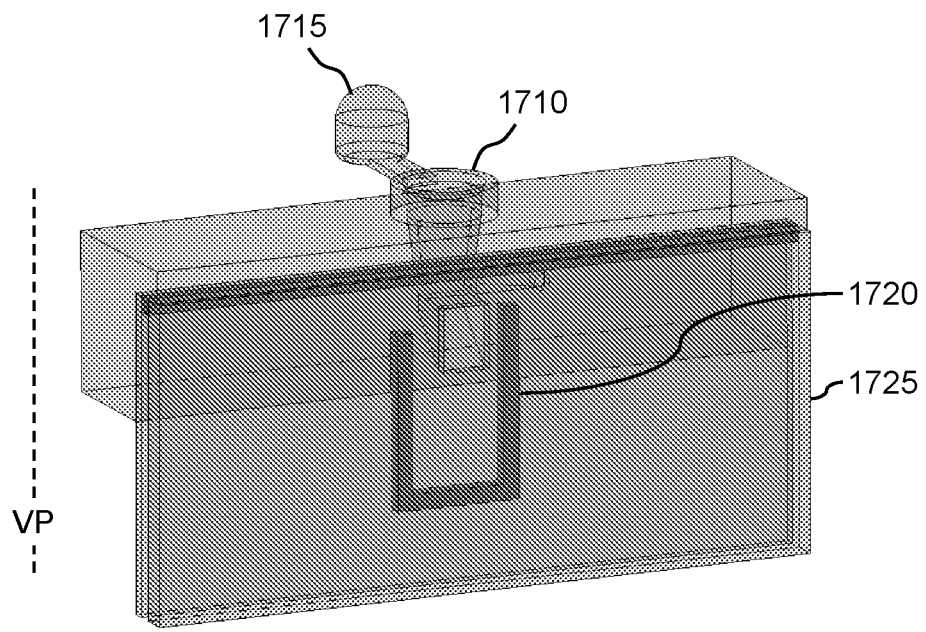
FIGS. 17A and 17B illustrate a perspective view and a cutaway perspective view, respectively, of another example of a loading port that can be used in the top edge of the presently disclosed fluidics cartridge that can be used in the vertical or substantially vertical position.
Figure 17B:
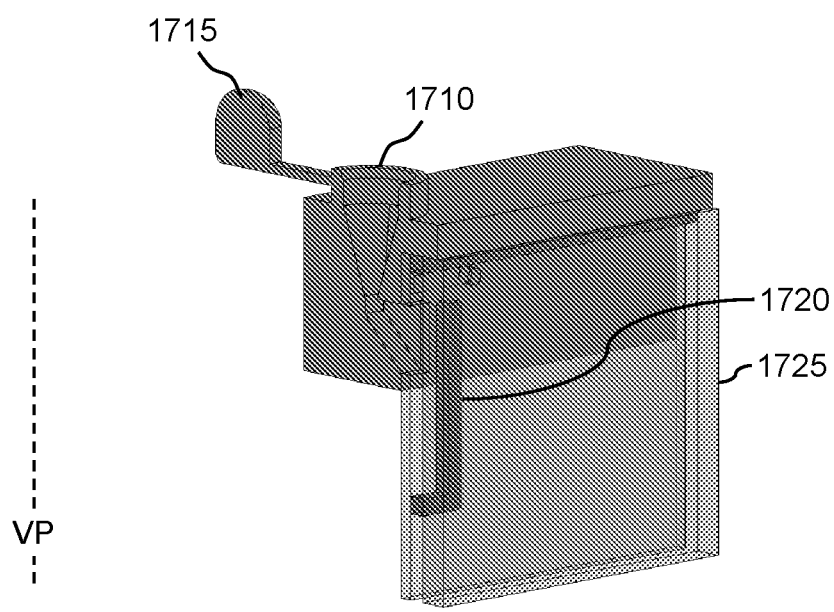

FIGS. 17A and 17B illustrate a perspective view and a cutaway perspective view, respectively, of another example of a loading port that can be used in the top edge of the presently disclosed fluidics cartridge that can be used in the vertical or substantially vertical position. Namely, FIGS. 17A and 17B show a loading port 1710 that has a cap 1715, wherein loading port 1710 can be located at the top edge of a fluidics cartridge that can be used in the vertical or substantially vertical position. Loading port 1710 is provided in relation to a U-channel 1720 and an off-cartridge reservoir 1725. In this example, using loading port 1710, the fluidics cartridge can loaded while in the vertical or substantially vertical position. In one configuration, a pipette (not shown) is inserted into loading port 1710. The shape of loading port 1710 can provide a stop for the body of the pipette. Then, upon withdrawal of the pipette, cap 1715 is secured on loading port 1710 to protect against leakage. In another configuration, the pipette can pass through a check valve (not shown) in loading port 1710, so the fluidics cartridge is protected against leakage through loading port 1710 after the pipette is withdrawn.

Systems

Some embodiments disclosed herein provide systems for conducting a reaction, comprising: a fluidic cartridge comprising a front substrate, a back substrate, and a plurality of electrodes configured to transport a droplet along a substantially vertical plane defined by the front substrate and the back substrate; and an instrument deck holding the fluidic cartridge in a substantially vertical position.

Figure 25:
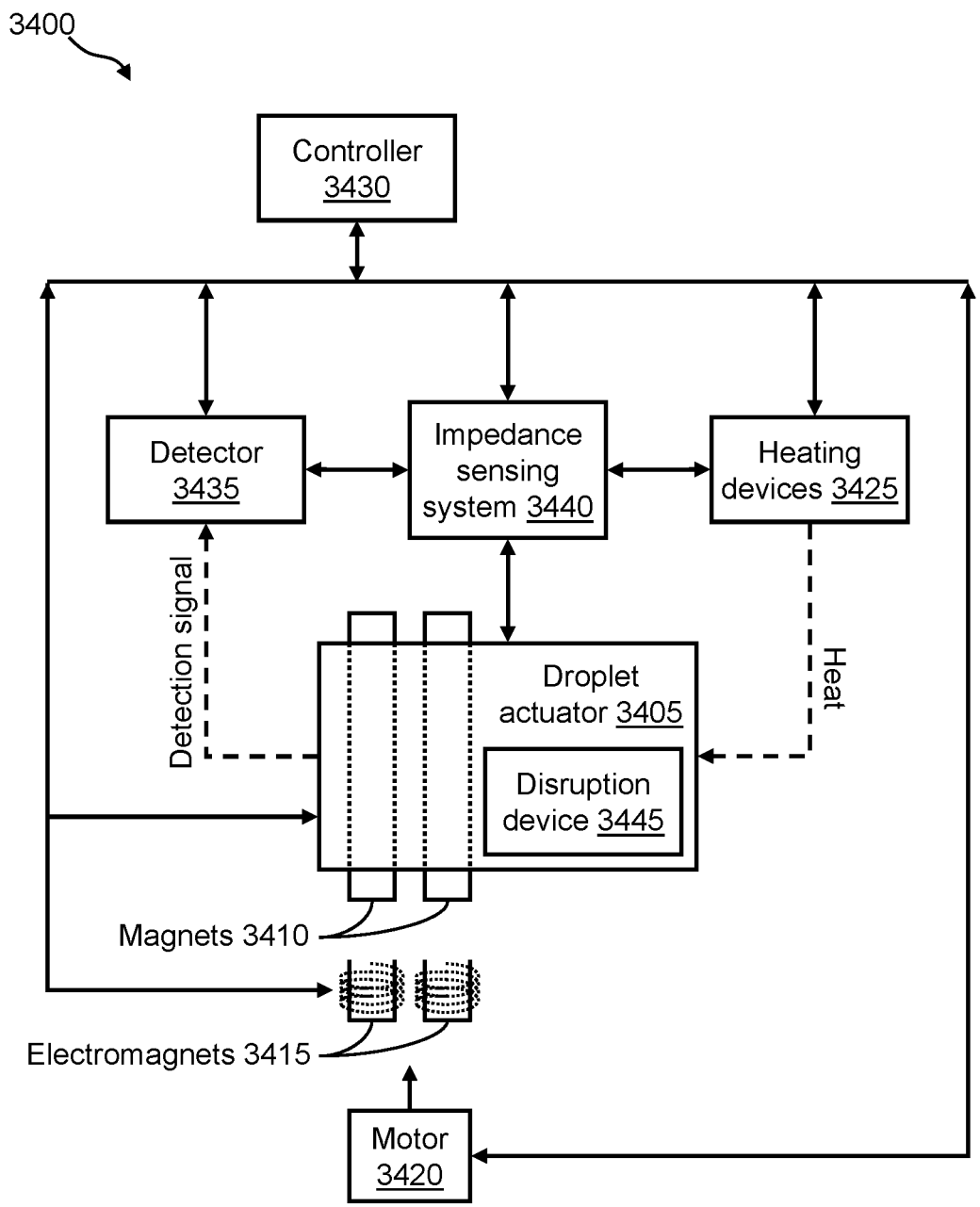
FIG. 25 illustrates a functional block diagram of an example of a microfluidics system that includes a droplet actuator, which is one example of a fluidics cartridge.

FIG. 25 illustrates a functional block diagram of an example of a microfluidics system 3400 that includes a droplet actuator 3405, which is one example of a fluidics cartridge. In microfluidics system 3400, droplet actuator 3405 can be a conventional horizontally-mounted droplet actuator or the presently disclosed fluidics cartridge (e.g., fluidics cartridge 300, 1500, 2700) that can be used in the vertical or substantially vertical position.

Digital microfluidic technology conducts droplet operations on discrete droplets in a droplet actuator, such as droplet actuator 3405, by electrical control of their surface tension (electrowetting). The droplets may be sandwiched between two substrates of droplet actuator 3405, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (i.e., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 3405 may be designed to fit onto an instrument deck (not shown) of microfluidics system 3400. The instrument deck may hold droplet actuator 3405 and house other droplet actuator features, such as, but not limited to, one or more magnets and one or more heating devices. For example, the instrument deck may house one or more magnets 3410, which may be permanent magnets. Optionally, the instrument deck may house one or more electromagnets 3415. Magnets 3410 and/or electromagnets 3415 are positioned in relation to droplet actuator 3405 for immobilization of magnetically responsive beads. Optionally, the positions of magnets 2610 and/or electromagnets 3415 may be controlled by a motor 3420. Additionally, the instrument deck may house one or more heating devices 3425 for controlling the temperature within, for example, certain reaction and/or washing zones of droplet actuator 3405. In one example, heating devices 3425 may be heater bars that are positioned in relation to droplet actuator 3405 for providing thermal control thereof.

A controller 3430 of microfluidics system 3400 is electrically coupled to various hardware components of the apparatus set forth herein, such as droplet actuator 3405, electromagnets 3415, motor 3420, and heating devices 3425, as well as to a detector 3435, an impedance sensing system 3440, and any other input and/or output devices (not shown). Controller 3430 controls the overall operation of microfluidics system 3400. Controller 3430 may, for example, be a general purpose computer, special purpose computer, personal computer, or other programmable data processing apparatus. Controller 3430 serves to provide processing capabilities, such as storing, interpreting, and/or executing software instructions, as well as controlling the overall operation of the system. Controller 3430 may be configured and programmed to control data and/or power aspects of these devices. For example, in one aspect, with respect to droplet actuator 3405, controller 3430 controls droplet manipulation by activating/deactivating electrodes.

In one example, detector 3435 may be an imaging system that is positioned in relation to droplet actuator 3405. In one example, the imaging system may include one or more light-emitting diodes (LEDs) (i.e., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in Banerjee et al., U.S. Pat. No. 8,241,573, entitled "Systems and Devices for Sequence by Synthesis Analysis," issued on Aug. 14, 2012; Feng et al., U.S. Pat. No. 7,329,860, entitled "Confocal Imaging Methods and Apparatus," issued on Feb. 12, 2008; Feng et al., U.S. Pat. No. 8,039,817, entitled "Compensator for Multiple Surface Imaging," issued on Oct. 18, 2011; Feng et al., U.S. Patent Pub. No. 20090272914, entitled "Compensator for Multiple Surface Imaging," published on Nov. 5, 2009; and Reed et al., U.S. Patent Pub. No. 20120270305, entitled "Systems, Methods, and Apparatuses to Image a Sample for Biological or Chemical Analysis," published on Oct. 25, 2012, the entire disclosures of which are incorporated herein by reference. Such detection systems are particularly useful for nucleic acid sequencing embodiments.

Impedance sensing system 3440 may be any circuitry for detecting impedance at a specific electrode of droplet actuator 3405. In one example, impedance sensing system 3440 may be an impedance spectrometer. Impedance sensing system 3440 may be used to monitor the capacitive loading of any electrode, such as any droplet operations electrode, with or without a droplet thereon. For examples of suitable capacitance detection techniques, see Sturmer et al., International Patent Pub. No. WO/2008/101194, entitled "Capacitance Detection in a Droplet Actuator," published on Dec. 30, 2009; and Kale et al., International Patent Pub. No. WO/2002/080822, entitled "System and Method for Dispensing Liquids," published on Feb. 26, 2004, the entire disclosures of which are incorporated herein by reference.

Droplet actuator 3405 may include disruption device 3445. Disruption device 3445 may include any device that promotes disruption (lysis) of materials, such as tissues, cells and spores in a droplet actuator. Disruption device 3445 may, for example, be a sonication mechanism, a heating mechanism, a mechanical shearing mechanism, a bead beating mechanism, physical features incorporated into the droplet actuator 3405, an electric field generating mechanism, armal cycling mechanism, and any combinations thereof. Disruption device 3445 may be controlled by controller 3430.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/ or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

Methods of Conducting a Reaction

Some embodiments disclosed herein provide methods of conducting a reaction using a fluidic cartridge, comprising: providing a reaction droplet to the droplet operations gap of the fluid cartridge; and actuating the reaction droplet to move vertically along the operations gap, wherein the fluidic cartridge is operated in a substantially vertical position.

A reaction droplet may be drawn from a reaction mixture located in the droplet operations gap, or created by mixing two or more droplets, e.g., a sample droplet, a reagent droplet, a buffer droplet, etc. A droplet may be drawn in any suitable way, for example, by downward dispense, by upward dispense, through an electrowetting array.

The methods and compositions disclosed herein may be used in a variety of nucleic acid applications, for example, hybridization, amplification, ligation, extension, washing, sequencing, etc. Common reagents are described in TruSeq® Enrichment Guide, Nextera® Enrichment Sample Preparation Guide, Nextera® Rapid Capture Enrichment Guide, TruSight™ Enrichment Sample Preparation Guide, MiSeq® Reagent Kit v3 Reagent Preparation Guide, HiSeq® Cluster Kit v4 Reference Guide, HiSeq® SBS Kit v4 Reference Guide, NextSeq® 500 System User Guide, TruSeq™ RNA Sample Preparation v2 Guide, Nextera XT DNA Library Preparation Guide, Nextera Mate Pair Sample Preparation Guide, TruSeq Nano DNA Sample Preparation Guide, TruSeq® Small RNA Sample Preparation Guide, TruSeq® Stranded mRNA Sample Preparation Guide, TruSeq® Stranded Total RNA Sample Preparation Guide, TruSeq® RNA Access Library Prep Guide, etc. (Illumina®, Inc., San Diego Calif.), which is incorporated by reference herein in its entirety. Common reagents and/or ingredients include one or more of the following: Resuspension Buffer (RSB), Nextera® Capture Target Buffer 1 (NCT1), Elute Target Buffer 1 (ET1), Elute Target Buffer 2 (ET2), Enrichment Hybridization Buffer (EHB), Enrichment Elution Buffer 1 (EE1), enrichment Wash Solution (EWS), Wash Solution 1 (WS1), Wash Solution 2 (WS2), Wash Solution 3 (WS3), PCR Master Mix (TC#-PMM), Nextera® Enrichment Amplification Mix (NEM), Nextera® Library Amplification Mix (NLM), HT1 Hybridisation buffer, HT2 Wash Buffer, PR1 Wash Buffer, PR2 Wash Buffer, PR3 Wash Buffer, SB1 Wash Buffer, SB2 Wash Buffer, SB3 Wash Buffer, USM Universal Scan Mix, SRE Scan Reagent, SRM Scan Reagent, BB2 Wash Buffer, BB3 Wash Buffer, BB4 Wash Buffer, LNW1 (Library Normalization Wash 1), LNS1 (Library Normalization Storage Buffer 1), RSB (Resuspension Buffer), BWB (Bead Wash Buffer), EPM Enhanced PCR Mix, ELB Elution Buffer, etc. (Illumina®, Inc., San Diego Calif.). In some embodiments, the reagents disclosed herein may comprise a DNA polymerase. In some embodiments, the reagents disclosed herein may comprise dNTPs. Other reagents include reagents common in nucleic acid applications, such as sample preparation and/or sequencing.

In some embodiments, a reagent comprising beads, such as magnetic beads may be used for the reactions disclosed herein. Therefore, disclosed herein are mechanisms of resuspending the beads in a reservoir or a droplet. In some embodiments, the beads may be resuspended by splitting and merging droplet for 10, 20, 30, 40, 50, 60, 70, 80, 90, 100 or more cycles. In some embodiments, the beads may be resuspended by an electromagnetic mixer. In some embodiments, the resuspension of beads is completed in a time interval that is, is about, is less than, 1 sec, 2 sec, 3 sec, 4 sec, 5 sec, 6 sec, 7 sec, 8 sec, 9 sec, 10 sec, 20 sec, 30 sec, 40 sec, 50 sec, 10 min, 20 min, 30 min, 40 min, 50 min, 60 min, 70 min, 80 min, 90 min, 100 min, or a range between any two of the above-mentioned values.

FIG. 7 illustrates an example of a process of performing droplet operations on the presently disclosed fluidics cartridge 300 that can be used in the vertical or substantially vertical position. FIG. 7 also illustrates an example of the aqueous/oil exchange process, wherein the filling of the reagent (e.g. reagent 362) into the filler fluid (e.g. filler fluid 360) is driven by capillary forces and gravity. By way of example, FIG. 7 shows a process of dispensing droplets 160 from one of the reagent U-features 318, then processing the dispensed droplets 160 along, for example, a PCR region, and then transporting the droplets 160 to waste; a process that relies on aqueous/oil exchange in fluidics cartridge 300.

For example, FIG. 7A shows droplets 160 being dispensed (via droplet operations) from reagent 362 that is in reagent U-feature 318D. Namely, droplets 160 are dispensed upward along the line or path of droplet operations electrodes 334. The droplets 160 are then transported (via droplet operations) and processed along a side-to-side line or path of droplet operations electrodes 334 in, for example, a PCR region of fluidics cartridge 300. Once processing is complete, the droplets 160 are transported (via droplet operations) to and then transporting the droplets 160 to waste U-feature 320. In this example, an aqueous/oil exchange process occurs between reagent U-feature 318D and reagent reservoir 356D. Namely, as droplets 160 are dispensed from reagent 362 in reagent U-feature 318D, the reagent volume that is removed from reagent U-feature 318D and reagent reservoir 356D is displaced with filler fluid 360 from oil reservoir 354. The local aqueous/oil exchange takes place via the upper flow path 336 and the lower flow path 338 associated with reagent U-feature 318D and reagent reservoir 356D. Similarly, as waste droplets are added to waste U-feature 320, aqueous/oil exchange takes place via the upper flow path 336 and the lower flow path 338 associated with waste U-feature 320 and waste reservoir 358. More details of the geometry to support aqueous/oil exchange in the presently disclosed fluidics cartridge are shown and described hereinbelow with reference to FIGS. 8, 9A, and 9B.

Over time, the volume of reagent 362 in reagent U-feature 318D and reagent reservoir 356D is depleted, while at the same time the amount of waste liquid 364 in waste U-feature 320 and waste reservoir 358 is increased. This is shown in FIGS. 7B, 7C, and 7D. With respect to droplets 160 collecting in waste U-feature 320, droplets 160 can be transported downward into waste U-feature 320 via droplet operations or droplets 160 can simply fall into waste U-feature 320 by gravity.

Downward Dispensing

In some embodiments, a droplet can be drawn by downward dispensing. In downward dispensing a reagent, a sample, a buffer, may be placed in a downward dispensing volume as disclosed herein. The downward dispensing volume may be porous or comprise opening at the bottom so that the liquid contained therein can be dispensed downward into the droplet operations gap. The downward dispensing volume may be connected to a blister, a reservoir or a sample loading port as disclosed herein, for example, through a flow path on the back substrate. Droplets may be dispensed downward from the downward dispensing volume by the force from one or more dispense electrodes, gravity, or a combination thereof. For example, gravity drives the downward dispensing volume toward the dispense electrodes, automatically replenishing this area without need for active electrowetting control to stage the reagents.

Various mechanisms for holding and delivering small volumes of reagent in the presently disclosed fluidics cartridge that can be used in the vertical or substantially vertical position. For example, they may be used for implementing a small reservoir inside a larger reservoir, such as the small reagent reservoirs 1554 inside the large-volume reservoir 1552 of fluidics cartridge 1500 as shown in FIGS. 15 and 16.

In some embodiments, a mechanism for holding and delivering small volumes of reagent in the presently disclosed fluidics cartridge can be used in the vertical or substantially vertical position. For example, a blister pack holding a small volume of liquid is provided inside a larger reservoir. One or more piercing elements are provided in relation to blister pack. A channel that runs through larger reservoir allows access to blister pack, whereby the blister pack is pushed against piercing elements and liquid is released. In some embodiments, the piercing elements may be microchip piercing elements or microchip barbs. In some embodiments, the blister pack can be implemented using, for example, bubble wrap technology. In some embodiments, the blister pack can be implemented using, for example, a kiss-cut type of blister pack. In some embodiments, the blister pack can be implemented using, for example, a frangible seal type of blister pack. In some embodiments, internal piercers may be used. For example, FIG. 18 shows an internal plaster pack with an internal piercer 1810 arranged therein.

The use of wax seals is another way of controlling when liquid is released in the presently disclosed fluidics cartridge that can be used in the vertical or substantially vertical position. For example, a wax seal-based valve in which a wax seal is located in a heating zone can be used. The flow path is initially sealed using the wax. Then heat is applied that melts the wax and permits flow. Preferably, the type of wax used is immiscible in the filler fluid and does not stay in suspension. In some embodiments, features can be designed into the fluidics cartridge for catching and trapping the wax once it has been melted and released into the flow. Preferably, the wax is a low melting temperature wax that is compatible with the chemistry used in the fluidic cartridge. In some embodiments, the wax may include an alkane wax, paraffin, wafer bonding wax, docosane, tricosane, or bleached bees wax, among others. In yet other embodiments, wax can be used to hold a ball in place, wherein the ball is positioned to block a flow port. Upon melting the wax, the ball drops by gravity, thereby opening the port to liquid flow.

One advantage of using a meltable wax is that it becomes easy to time the release without needing complex mechanical actuators. Further, using a meltable wax allows the timing to be varied from application to application without any hardware changes. Further, the use of mechanical actuators to break seals forces the blister packs to always be in the same locations, which can be limiting. By contrast, meltable wax can placed anywhere, which can vary from application to application. Also, meltable wax may allow blister packs to be placed anywhere.

The use of phase change actuators is another way of controlling when liquid is released in the presently disclosed fluidics cartridge that can be used in the vertical or substantially vertical position. For example, a wax-based phase change actuator may be used. Generally, the operation of phase change actuators is based on expansion. In wax-based phase change actuator, volumetric expansion on the order of 8-15% is used to open or close an elastomeric valve. The valve can be designed to be normally open or normally closed. A wax-based phase change actuator may be particularly useful for the large-volume reservoirs, such as large-volume reservoir 1552 of fluidics cartridge 1500.

Droplet Exchange over CMOS

In some embodiments, a droplet can be detected by moving across a CMOS detector that is flush mounted in a fluidics cartridge as disclosed herein. For example, the CMOS detector may be mounted along an electrowetting path, so that a droplet moving along the electrowetting path can move across the CMOS detector. In some embodiments, the droplet may move across the CMOS detector as a result of gravity, by the force of one or more electrodes on the electrowetting path, or a combination thereof. In some embodiments, the CMOS detector may be mounted on the back substrate, wherein the droplet may be moved across the CMOS detector by the force of one or more electrodes mounted on the front substrate, or vice versa.

Certain aspects of present disclosure are described with reference to various methods and method steps. It will be understood that each method step can be implemented by the program code and/or by machine instructions. The program code and/or the machine instructions may create means for implementing the functions/acts specified in the methods.

Sequencing Methods

The devices, systems and methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference in their entireties. This approach is being commercialized by Solexa (now Illumina Inc.), and is also described in International Patent Pub. No. WO 91/06678 and International Patent Pub. No. WO 07/123,744, the disclosures of which are incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference in its entirety). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057,026, U.S. Patent Pub. No. 2006/0240439, U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. Patent Pub. No. 2012/0270305 and U.S. Patent Pub. No. 2013/0260372, the disclosures of each of which are incorporated herein by reference in its entirety.

Some embodiments can utilize detection of four different nucleotides using fewer than four different labels. For example, SBS can be performed utilizing methods and systems described in U.S. Patent Pub. No. 2013/0079232, which is incorporated herein by reference in its entirety. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated disclosure of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation (SBL) techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBL systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference in its entirety) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Pub. No. 2008/0108082 (each of which is incorporated herein by reference in its entirety). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference in its entirety. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at a density that is, is about, is less than, or is more than, 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or a density that is a range between any of these values, for example, 10 features/cm$^2$ to 5,000,000 features/cm$^2$, 100 features/cm$^2$ to 1,000,000 features/cm$^2$, 500 features/cm$^2$ to 100,000 features/cm$^2$, 1,000 features/cm$^2$ to 50,000 features/cm$^2$, 5,000 features/cm$^2$ to 10,000 features/cm$^2$, etc.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference in its entirety. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference in its entirety.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

All publications, including patent documents and scientific articles, referred to in this application and the bibliography and attachments are incorporated by reference for the referenced materials and in their entireties for all purposes to the same extent as if each individual publication were individually incorporated by reference.

Citation of the above publications or documents is not intended as an admission that any of the foregoing is pertinent prior art, nor does it constitute any admission as to the contents or date of these publications or documents.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

Terms and phrases used in this document, and embodiments thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless apparent from the context or expressly stated otherwise. Similarly, a group of items linked with the conjunction "or" should not be read as requiring mutual exclusivity among that group, but rather should also be read as "and/or" unless it is apparent from the context or expressly stated otherwise. Furthermore, although items, elements or components of the invention may be described or claimed in the singular, the plural is contemplated to be within the scope thereof unless limitation to the singular is explicitly stated. For example, "at least one" may refer to a single or plural and is not limited to either. The presence of broadening words and phrases such as "one or more," "at least," "but not limited to", or other like phrases in some instances shall not be read to mean that the narrower case is intended or required in instances where such broadening phrases may be absent.

What is claimed is:

1. A fluidics cartridge for use in a substantially vertical position comprising:
    (a) a front substrate;
    (b) a back substrate;
    (c) a droplet operations gap formed between the front substrate and the back substrate; and
    (d) a plurality of electrodes on the front substrate or the back substrate,
    wherein the plurality of electrodes is configured to transport a droplet along a substantially vertical plane defined by the front substrate and the back substrate;
    wherein the front substrate comprises at least one U-feature which comprises a U-shaped protrusion from an inside surface of the front substrate and which is configured to hold a sample, a reaction mixture, a reagent, a filler fluid, a buffer, or a waste liquid.

2. The fluidics cartridge of claim 1, wherein the front substrate or the back substrate is a printed circuit board (PCB).

3. The fluidics cartridge of claim 1, wherein the back substrate comprises one or more flow paths.

4. The fluidics cartridge of claim 1, comprising one or more reservoirs configured to hold a reagent, a filler fluid, a buffer, or a waste liquid.

5. The fluidics cartridge of claim 4, wherein the one or more reservoirs can hold a volume of 1-100 ml.

6. The fluidics cartridge of claim 4, wherein the one or more reservoirs are integrated into a plate to form a reservoir assembly.

7. The fluidics cartridge of claim 4, wherein each of the one or more reservoirs is in fluid communication with the droplet operations gap through a flow path.

8. The fluidics cartridge of claim 4, wherein each of the one or more reservoirs are in fluid communication with the droplet operations gap through an upper flow path and a lower flow path.

9. The fluidics cartridge of claim 4, wherein the one or more reservoirs comprise a U-shaped portion.

10. The fluidics cartridge of claim 3, wherein the height of the droplet operations gap at the position of a flow path is greater than the height of the droplet operations gap.

11. The fluidics cartridge of claim 1, wherein a U-feature corresponds to a reservoir.

12. The fluidics cartridge of claim 11, wherein each of the one or more U-features comprises a U-shaped protrusion from an inside surface of the front substrate.

13. The fluidics cartridge of claim 12, wherein the U-shaped protrusion is porous.

14. The fluidics cartridge of claim 12, wherein the height of the U-shaped protrusion equals the height of the droplet operations gap.

15. The fluidics cartridge of claim 1, wherein the front substrate or back substrate comprises one or more downward dispensing volumes configured to hold a sample, a reaction mixture, a reagent, or a buffer.

16. The fluidics cartridge of claim 15, wherein the one or more downward dispensing volumes comprise sections having different heights.

17. The fluidics cartridge of claim 1, wherein the plurality of electrodes is configured to transport a droplet from the one or more U-features or the one or more downward dispensing volumes.

18. The fluidics cartridge of claim 17, wherein the plurality of electrodes is configured to form an electrowetting array.

19. The fluidics cartridge of claim 18, wherein the electrowetting array comprises a reagent dispense region, a reaction region, a sample loading region, a waste collection region, and a detection region.

20. The fluidics cartridge of claim 19, wherein the detection region comprises a CMOS detector.

21. The fluidics cartridge of claim 19, wherein the reaction region is configured to conduct a nucleic acid reaction selected from the group consisting of a PCR reaction, a sequencing reaction, a primer extension reaction and a clustering reaction.

22. A method of conducting a reaction using the fluidic cartridge according to claim 1, comprising:
    providing a reaction droplet to the droplet operations gap of the fluid cartridge; and
    actuating the reaction droplet to move vertically along the operations gap,
    wherein the fluidic cartridge is operated in a substantially vertical position.

23. The method of claim 22, comprising drawing the reaction droplet by downward dispensing or upward dispensing.

24. The method of claim 22, comprising activating a CMOS detector to detect a reaction product in the reaction droplet.

25. The method of claim 22, comprising filling the droplet operations gap by passive refill.

26. The method of claim 22, comprising resuspending a plurality of beads in the droplet.

27. A system for conducting a reaction, comprising:
    a fluidic cartridge comprising a front substrate, a back substrate, and a plurality of electrodes configured to transport a droplet along a substantially vertical plane defined by the front substrate and the back substrate, wherein the front substrate comprises at least one U-feature which comprises a U-shaped protrusion from an inside surface of the front substrate and which is configured to hold a sample, a reaction mixture, a reagent, a filler fluid, a buffer, or a waste liquid; and
    an instrument deck holding the fluidic cartridge in a substantially vertical position.

* * * * *

UNITED STATES PATENT AND TRADEMARK OFFICE
CERTIFICATE OF CORRECTION

PATENT NO. : 10,576,471 B2
APPLICATION NO. : 15/559321
DATED : March 3, 2020
INVENTOR(S) : James Osmus et al.

It is certified that error appears in the above-identified patent and that said Letters Patent is hereby corrected as shown below:

On the Title Page

Column 1, (87) PCT Pub. No., delete "WO2015/154038" and insert -- WO2016/154038 --, therefor.

Signed and Sealed this
Twenty-sixth Day of May, 2020

Andrei Iancu
*Director of the United States Patent and Trademark Office*